US010268966B2

(12) United States Patent
Mould

(10) Patent No.: US 10,268,966 B2
(45) Date of Patent: *Apr. 23, 2019

(54) SYSTEM AND METHOD FOR PROVIDING PATIENT-SPECIFIC DOSING AS A FUNCTION OF MATHEMATICAL MODELS UPDATED TO ACCOUNT FOR AN OBSERVED PATIENT RESPONSE

(71) Applicant: Diane R. Mould, Fort Myers, FL (US)

(72) Inventor: Diane R. Mould, Fort Myers, FL (US)

(73) Assignee: Diane R. Mould, Fort Myers, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/730,112

(22) Filed: Oct. 11, 2017

(65) Prior Publication Data

US 2018/0032892 A1   Feb. 1, 2018

Related U.S. Application Data

(63) Continuation of application No. 14/457,601, filed on Aug. 12, 2014, which is a continuation of application
(Continued)

(51) Int. Cl.
*G01N 33/48* (2006.01)
*G06N 7/00* (2006.01)
(Continued)

(52) U.S. Cl.
CPC ............. *G06N 7/005* (2013.01); *G06F 19/00* (2013.01); *G06F 19/3456* (2013.01); *G16H 20/10* (2018.01); *G16H 50/50* (2018.01)

(58) Field of Classification Search
None
See application file for complete search history.

(56) References Cited

U.S. PATENT DOCUMENTS 5,365,948 A   11/1994   McMichael
5,542,436 A    8/1996   McMichael
(Continued)

FOREIGN PATENT DOCUMENTS

WO   WO-2011059824 A2   5/2011
WO   WO-2014173558 A1   10/2014

OTHER PUBLICATIONS

AMA, Evaluation of medical information science in medical education, National Library of Medicine, pp. 518-519 (Jan. 23, 1986) (58 pages).
(Continued)

*Primary Examiner* — Larry D Riggs, II
(74) *Attorney, Agent, or Firm* — White & Case LLP

(57) ABSTRACT

A system and method for predicting, proposing and/or evaluating suitable medication dosing regimens for a specific individual as a function of individual-specific characteristics and observed responses of the specific individual. Mathematical models of observed patient responses are used in determining an initial dose. The system and method use the patient's observed response to the initial dose to refine the model for use to forecast expected responses to proposed dosing regimens more accurately for a specific patient. More specifically, the system and method uses Bayesian averaging, Bayesian updating and Bayesian forecasting techniques to develop patient-specific dosing regimens as a function of not only generic mathematical models and patient-specific characteristics accounted for in the models as covariate patient factors, but also observed patient-specific responses that are not accounted for within the models themselves, and that reflect variability that distinguishes the specific patient from the typical patient reflected by the model.

20 Claims, 16 Drawing Sheets

Related U.S. Application Data

No. 14/047,545, filed on Oct. 7, 2013, now Pat. No. 10,083,400.

(60) Provisional application No. 61/710,330, filed on Oct. 5, 2012.

(51) Int. Cl.
*G06F 19/00* (2018.01)
*G16H 50/50* (2018.01)
*G16H 20/10* (2018.01)

(56) References Cited

U.S. PATENT DOCUMENTS

| | | | |
|---|---|---|---|
| 5,694,950 | A | 12/1997 | McMichael |
| 6,267,116 | B1 | 7/2001 | McMichael |
| 6,575,169 | B2 | 6/2003 | McMichael |
| 6,578,582 | B2 | 6/2003 | McMichael |
| 6,581,606 | B2 | 6/2003 | Kutzko et al. |
| 6,581,607 | B2 | 6/2003 | Kutzko et al. |
| 6,883,521 | B2 | 4/2005 | McMichael |
| 6,942,614 | B1 | 9/2005 | Kutzko et al. |
| 8,589,175 | B2 | 11/2013 | Glauser et al. |
| 2004/0122719 | A1 | 6/2004 | Sabol et al. |
| 2004/0122790 | A1 | 6/2004 | Walker et al. |
| 2005/0187789 | A1 | 8/2005 | Hatlestad et al. |
| 2006/0036619 | A1* | 2/2006 | Fuerst ............... G06Q 10/10 |
| 2008/0124689 | A1 | 5/2008 | Williams et al. |
| 2008/0188763 | A1 | 8/2008 | John et al. |
| 2008/0301077 | A1 | 12/2008 | Fung et al. |
| 2010/0273738 | A1 | 10/2010 | Valcke et al. |
| 2011/0184267 | A1 | 7/2011 | Duke et al. |
| 2011/0306845 | A1 | 12/2011 | Osorio |
| 2011/0306846 | A1 | 12/2011 | Osorio |
| 2014/0114676 | A1 | 4/2014 | Holmes |
| 2014/0379629 | A1 | 12/2014 | Loew-Baselli et al. |

OTHER PUBLICATIONS

Anderson, et al., "Clinical Pharmacokinetics Computer Programs," In: Pharmacy Informatics, Bourne, CRC Press (2010), pp. 199-216.
Angelier, Evaluation of a nenatal hyperalimentation microcomputer program, The University of Arizona, pp. 79, 84 (1988) (255 pages).
Anonymous: "Bayesian inference," Wikipedia, Oct. 2, 2012 (Oct. 2, 2012), XP055380922, Retrieved from the Internet: URL:https://en.wikipedia.otg/w/index.php?title=Bayesian_inferenced&oldid=515620785 [retrieved on Jun. 13, 2017].
Anonymous: "Ensemble learning," Wikipedia, Aug. 23, 2012, Retrieved from the Internet: URL:https://en.wikipedia.org/w/index.php?title=Ensemble_learning&oldid=508782155.
Assenmacher-Wesche and Pesaran, Forecasting the Swiss economy using VECX models: an exercise in forecast combination across modeals and obsrevation windows, National Institute Economic Review No. 203, 18 pages (Jan. 2008).
Blau et al. "A Bayesian Pharmacometric Approach for Personalized Medicine—A Proof of Concept Study With Simulated Data" IEEE 2009 p. 1969-1976.
Fasanmade et al., "Population pharmacokinetic analysis of infliximab in patients with ulcerative colitis," Eur J Clin Pharmacal., 65:1211-1228 (2009).
Goel, Application of an active comparator-based benefit-risk assessment in evaluating clinical trial design features of a new chemical entity using a Bayesian decision-theorectic framework, a dissertation submitted to the faculty of the Graduate School of the University of Minnesota, pp. 17-36 (Jun. 2010) (142 pages).
http://doseme.eom.au/index.html, retrived from the Internet on Nov. 5, 2014, pp. 1-3.
http://pkb.chop.edu/index.php, retrieved from the Internet on Nov. 5, 2014, pp. 1-3.
http://www.firstdose.org/, retrieved from the Internet on Nov. 5, 2014, 1 page.
http://www.laQk.org/RiqhtDose_manuaL_pdf, retrieved from the Internet on Nov. 10, 2014, pp. 1-114.
http://www.mediware.cz/index_en.html, retrieved from the Internet on Nov. 5, 2014, pp. 1-2.
http://www.meds.com/DoseCalc/dcintro.html, retrieved from the Internet on Nov. 10, 2014, pp. 1-2.
http://www.rxkinetics.com/, retrieved from the Internet on Nov. 5, 2014, one paQe.
http://www.tciworks.info/, retrieved from the Internet on Nov. 5, 2014, pQs 1-3.
http://www.tdms2000.com/, retrieved from the Internet on Nov. 5, 2014, pp. 1-2.
http://www.testandcalc.com/drugcalc/index.asp, retrieved from Internet on Nov. 5, 2014, pp. 1-2.
http://www.warfarindosing.org/Source/Home.aspx, retrieved from the Internet on Nov. 5,.2014, one paQe.
International Preliminary Report on Patentability and Written Opinion in International Application No. PCT/US2013/063691 dated Apr. 16, 2015.
International Search Report and Written Opinion for International Application No. PCT/US2016/026562 dated Jul. 18, 2016.
International Search Report for International Application No. PCT/US2013/063691 dated Mar. 5, 2014.
Montazeri, Ashraf, et al., "Individual Adaptive Dosing of Topotecan in Ovarian Cancer," Clin Cancer Res Feb. 2002;8:394-399 (downloaded from clincancerres.aacrjournals.org on Jul. 7, 2012).
Mould et al., "Basic concepts in population modeling, simulations, and model-based drug development," Pharmacometrics & Systems Pharamacology, 1, e6 (2012) (14 pages).
Mould, et al "Dashboard Systems: Pharmacokinetic/Pharmacodynamic Mediated Dose Optimization for Monoclonal Antibodies," The Journal of Clinical Pharmacology, 55:83, published online Feb. 23, 2015, pp. S51-S59.
Mould, et al, "Dashboard Systems: Implementing Pharmacometrics from Bench to Bedside," The AAPS Journal, 16:5, Sep. 2014, pp. 925-937.
Tobler, Andrea et al., "Intravenous phenytoin: a retrospective analysis of Bayesian forecasting versus conventional dosing in patients," Int J Clin Pharm (Jun. 29, 2013) 35:790-797.
Wallin, Johan: "Dose Adaptation Based on Pharmacometric; Models" In: "Dose Adaptation Based on Pharmacometric; Models", Jan. 1, 2009 (Jan. 1, 2009), Uppsala: Acta; Universitatis Upsaliensis, Uppsala, Sweden, XP055271184,; ISSN: 1651-6182, ISBN: 978-91-5-547488-1.
Yin et al., "Bayesian model averaging continual reassessment method in Phase 1 clinical trials," Journal of the American Statistical Association, 104:954-968 (2009).
Ahnstrom, et al., "A 6-year follow-up of dosing, coagulation factor levels and bleedings in relation to joint status in the prophylactic treatment of haemophilia," Haemophilia, 10, pp. 689-697 (2004).
Bjorkman, et al., "Population pharmacokinetics of recombinant factor VIII: the relationships of pharmacokinetics to age and body weight," Blood, 119, pp. 612-618 (2012).
Bjorkman, S. "Limited Blood Sampling for Pharmacokinetic Dose Tailoring of FVIII in the Prophylactic Treatment of Haemophilia A," Haemophilia, 16, pp. 597-605 (2010).
Bjorkman, S. "Prophylactic Dosing of Factor VIII and Factor XI from a Clinical Pharmacokinetic Perspective," Haemophilia, 9, pp. 101-110 (2003).
Carlsson, et al., "Pharmacokinetic Dosing in Prophylactic Treatment of Hemophilia A," European Journal of Haematology, 51, pp. 247-252 (1993).
Collins, et al., "Factor VIII requirement to maintain a target plasma level in the prophylactic treatment of severe hemophilia A: influences of variance in pharmacokinetics and treatment regimens," Journal of Thrombosis and Haemostasis, 8, pp. 269-275 (2009).
Collins, et al., "Implications of coagulation Factor VIII and IX Pharmacokinetics in the Prophylactic Treatment of Haemophilia," Haemophilia, 17 pp. 2-10 (2011).
Jelliffe, et al., "Individualizing Drug Dosage Regimens: Roles of Population Pharmacokinetic and Dynamic Models, Bayesian Fitting, and Adaptive Control," Therapeutic Drug Monitoring, 15, pp. 380-393 (1993).

(56) References Cited

OTHER PUBLICATIONS

Ljung, Rolf, "Prophylactic Therapy in Haemophilia," Blood Reviews, 23, pp. 267-274 (2009).

* cited by examiner

−1.17

−0.911

0.670

1.24

SYSTEM AND METHOD FOR PROVIDING PATIENT-SPECIFIC DOSING AS A FUNCTION OF MATHEMATICAL MODELS UPDATED TO ACCOUNT FOR AN OBSERVED PATIENT RESPONSE

This application is a continuation of U.S. patent application Ser. No. 14/457,601 filed on Aug. 12, 2014, which is a continuation of U.S. patent application Ser. No. 14/047,545 filed on Oct. 7, 2013, which claims the benefit under 35 U.S.C. § 119(e) of U.S. Provisional Application No. 61/710,330, filed on Oct. 5, 2012, each of which is incorporated by reference herein in its entirety.

FIELD OF THE INVENTION

The present invention relates generally to the administration of medications to live patients. More particularly, the present invention relates to a computerized system and method for processing medication-specific mathematical models in view of observed patient-specific responses to predict, propose and/or evaluate suitable medication dosing regimens for a specific patient.

BACKGROUND OF THE INVENTION

A physician's decision to start a patient on a medication-based treatment regimen involves development of a dosing regimen for the medication to be prescribed. Different dosing regimens will be appropriate for different patients having differing patient factors. By way of example, dosing quantities, dosing intervals, treatment duration and other variables may be varied. Although a proper dosing regimen may be highly beneficial and therapeutic, an improper dosing regimen may be ineffective or deleterious to the patient's health. Further, both under-dosing and over-dosing generally results in a loss of time, money and/or other resources, and increases the risk of undesirable outcomes.

In current clinical practice, the physician typically prescribes a dosing regimen based on dosing information contained in the package insert (PI) of the prescribed medication. In the United States, the contents of the PI are regulated by the Food and Drug Administration (FDA). As will be appreciated by those skilled in the art, the PI is typically a printed informational leaflet including a textual description of basic information that describes the drug's appearance, and the approved uses of the medicine. Further, the PI typically describes how the drug works in the body and how it is metabolized. The PI also typically includes statistical details based on trials regarding the percentage of people who have side effects of various types, interactions with other drugs, contraindications, special warnings, how to handle an overdose, and extra precautions. PIs also include dosing information. Such dosing information typically includes information about dosages for different conditions or for different populations, like pediatric and adult populations. Typical PIs provide dosing information as a function of certain limited patient factor information. Such dosing information is useful as a reference point for physicians in prescribing a dosage for a particular patient.

FIG. 1 is a flow diagram 100 illustrating a method for developing a medication dosing regimen for a patient that is exemplary of the prior art. As shown in FIG. 1, a typical method involves identifying a patient having patient factors specified in the PI, and then for the selected medication that the physician is choosing to prescribe, reviewing the PI dosing information, as shown at steps 102 and 104 of Figure.

By way of example, PI dosing information for Diovan® brand valsartin, an angiotensin receptor blocker used in adults to treat high blood pressure, heart failure, etc., which is manufactured and/or distributed by Novartis Corporation of Summit, N.J., USA provides, in part, the following dosing information: the type of patient for whom the medication is suitable (hypertensive patients), the types of patients for whom the drug should not be used (pregnant women, patients who are volume or salt-depleted), a recommended initial dose (80 mg), a recommended does interval (once daily), and the approved range of doses that may be legally and/or ethically prescribed (80 to 320 mg).

Such dosing information is typically developed by the medication's manufacturer, after conducting clinical trials involving administration of the drug to a population of test subjects, carefully monitoring the patients, and recording of clinical data associated with the clinical trial. The clinical trial data is subsequently compiled and analyzed to develop the dosing information for inclusion in the PI. Systems, methods, process and techniques for gathering, compiling and analyzing data to develop dosing information for inclusion in a PI are well-known in the art and beyond the scope of the present invention, and thus are not discussed in detail herein.

It should be noted that the typical dosing information is in a sense a generic reduction or composite, from data gathered in clinical trials of a population including individuals having various patient factors, that is deemed to be suitable for an "average" patient having "average" factors and/or a "moderate" level of disease, without regard to many of any specific patient's factors, including some patient factors that may have been collected and tracked during the clinical trial. By way of example, based on clinical trial data gathered for Abatacept, an associated PI provides indicated dosing regimens with a very coarse level of detail—such as 3 weight ranges (<60 kg, 60-100 kg, and >100 kg) and associated indicated dosing regimens (500 mg, 750 mg and 1000 mg, respectively). Such a coarse gradation linked to limited patient factors (e.g., weight), ignores many patient-specific factors that could impact the optimal or near-optimal dosing regimen. Accordingly, it is well-understood that a dosing regimen recommended by a PI is not likely to be optimal or near-optimal for any particular patient, but rather provides a safe starting point for treatment, and it is left to the physician to refine the dosing regimen for a particular patient, largely through a trial-and-error process.

Nevertheless, the physician then determines an indicated dosing regimen for the patient as a function of the PI information, as shown at step 106. For example, the indicated dosing regimen may be determined to be 750 mg, every 4 weeks, for a patient having a weight falling into the 60-100 kg weight range. The physician then administers the indicated dosing regimen as shown at 108. It will be appreciated that this may be performed directly or indirectly, e.g., by prescribing the medication, causing the medication to be administered and/or administering a dose to the patient consistent with the dosing regimen.

As referenced above, the indicated dosing regimen may be a proper starting point for treating a hypothetical "average" patient, the indicated dosing regimen is very likely not the optimal or near-optimal dosing regimen for the specific patient being treated. This may be due, for example, to the individual factors of the specific patient being treated (e.g., age, concomitant medications, other diseases, renal function, etc.) that are not captured by the parameters accounted for by the PI (e.g., weight). Further, this may be due to the coarse stratification of the recommended dosing regimens (e.g., in 40 kg increments), although the proper dosing is more likely a continuously variable function of one or more patient factors.

Current clinical practice acknowledges this discrepancy. Accordingly, it is common clinical practice to follow-up with a patient after an initial dosing regimen period to re-evaluate the patient and dosing regimen. Accordingly, as shown in FIG. 1, the physician next evaluates the patient's response to the indicated dosing regimen, as shown at 110. By way of example, this may involve examining the patient, drawing blood or administering other tests to the patient and/or asking for patient feedback, such that the patient's response to the previously-administered dosing regimen may be observed by the treating physician. As a result of the evaluation and observed response, the physician determines whether a dose adjustment is warranted, e.g., because the patient response is deficient, as shown at step 112. Such a determination may be made in accordance with existing medical treatment practices and is beyond the scope of the present invention, and thus not discussed here.

If it is determined at step 112 that a dose adjustment is not warranted, then the physician may discontinue dosing adjustments and the method may end, as shown at steps 112 and 118.

If, however, it is determined at step 112 that a dose adjustment is warranted, then the physician will adjust the dosing regimen ad hoc, as shown at 114. Sometimes the suitable adjustment is made solely in the physician's judgment. Often, the adjustment is made in accordance with a protocol set forth in the PI or by instructional practice. By way of example, the PI may provide quantitative indications for increasing or decreasing a dose, or increasing or decreasing a dosing interval. In either case, the adjustment is made largely on an ad hoc basis, as part of a trial-and-error process, and based largely on data gathered after observing the effect on the patient of the last-administered dosing regimen.

After administering the adjusted dosing regimen, the patient's response to the adjusted dosing regimen is evaluated, as shown at step 116. The physician then again determines whether to adjust the dosing regimen, as shown at 118, and the process repeats.

Such a trial-and-error based approach relying on generic indicated dosing regimens and patient-specific observed responses works reasonably well for medications with a fast onset of response. However, this approach is not optimal, and often not satisfactory, for drugs that take longer to manifest a desirable clinical response. Further, a protracted time to optimize dosing regimen puts the patient at risk for undesirable outcomes.

What is needed is system and method for predicting, proposing and/or evaluating suitable medication dosing regimens for a specific individual as a function of individual-specific characteristics that eliminates or reduces the trial-and-error aspect of conventional dosing regimen development, and that shortens the length of time to develop a satisfactory or optimal dosing regimen, and thus eliminates or reduces associated waste of medications, time or other resources and reduces the risk of undesirable outcomes.

SUMMARY

The present invention provides a system and method for providing patient-specific medication dosing as a function of mathematical models updated to account for an observed patient response. More specifically, the present invention provides a system and method for predicting, proposing and/or evaluating suitable medication dosing regimens for a specific individual as a function of individual-specific characteristics and observed responses of the specific individual to the medication.

Conceptually, the present invention provides access, in a direct way, to mathematical models of observed patient responses to a medication. In prescribing an initial dose, the present invention allows for use of published mathematical model(s) to predict a specific patient's response as a function of patient-specific characteristics that are account for in the model(s) as patient factor covariates. Accordingly, the prescribing physician is able to leverage the model(s) in developing a reasonably tailored initial dose for a specific patient, as a function of the specific patient's characteristics, with much greater precision than a PI can provide.

To account for this uniqueness of any particular patient (BSV), the present invention allows for further use of the specific patient's observed response to the initial dosing regimen to adjust the dosing regimen. Specifically, the inventive system and method uses the patient's observed response in conjunction with the published mathematical model(s) and patient-specific characteristics to account for BSV that cannot be accounted for by the mathematical models alone. Accordingly, the present invention allows observed responses of the specific patient to be used refine the models and related forecasts, to effectively personalize the models so that they may be used to forecast expected responses to proposed dosing regimens more accurately for a specific patient. By using the observed response data to personalize the models, the models are modified to account for between-subject variability (BSV) that is not accounted for in conventional mathematical models, which described only typical responses for a patient population, or a "typical for covariates" response for a typical patient having certain characteristics accounted for as covariates in the model.

Conceptually, the present invention allows the prescribing physician to develop a personalized dosing regimen using one or more published mathematical models reflecting actual clinical data, without the loss of resolution in the data and/or model that results from distillation of the actual clinical data into a relatively coarsely stratified set of recommendations for an "average" or "typical" patient, as in a PI.

The model-based development of such patient-specific medication dosing regimens eliminates or reduces the trial-and-error aspect of conventional dosing regimen development. Further, such model-based development shortens the length of time to develop a satisfactory or optimal dosing regimen, and thus eliminates or reduces associated waste of medications, time or other resources, as well as reduces the amount of time that a patient is at risk of undesirable outcomes.

Generally, the system and method involves gathering of mathematical models developed from clinical data gathered from patients to whom a particular medication had been administered, processing the models to create a composite model rich in patient data, and determining patient-specific dosing regimens as a function of patient-specific observed response data processed in conjunction with data from the mathematical model(s). More specifically, the system and method uses Bayesian averaging, Bayesian updating and Bayesian forecasting techniques to develop patient-specific dosing regimens as a function of not only generic mathematical models and patient-specific characteristics accounted for in the models as covariate patient factors, but also observed patient-specific responses that are not accounted for within the models themselves, and that reflect BSV that distinguishes the specific patient from the typical patient reflected by the model.

BRIEF DESCRIPTION OF THE DRAWINGS

An understanding of the following description will be facilitated by reference to the attached drawings, in which.

DETAILED DESCRIPTION OF THE INVENTION

Figure 1:
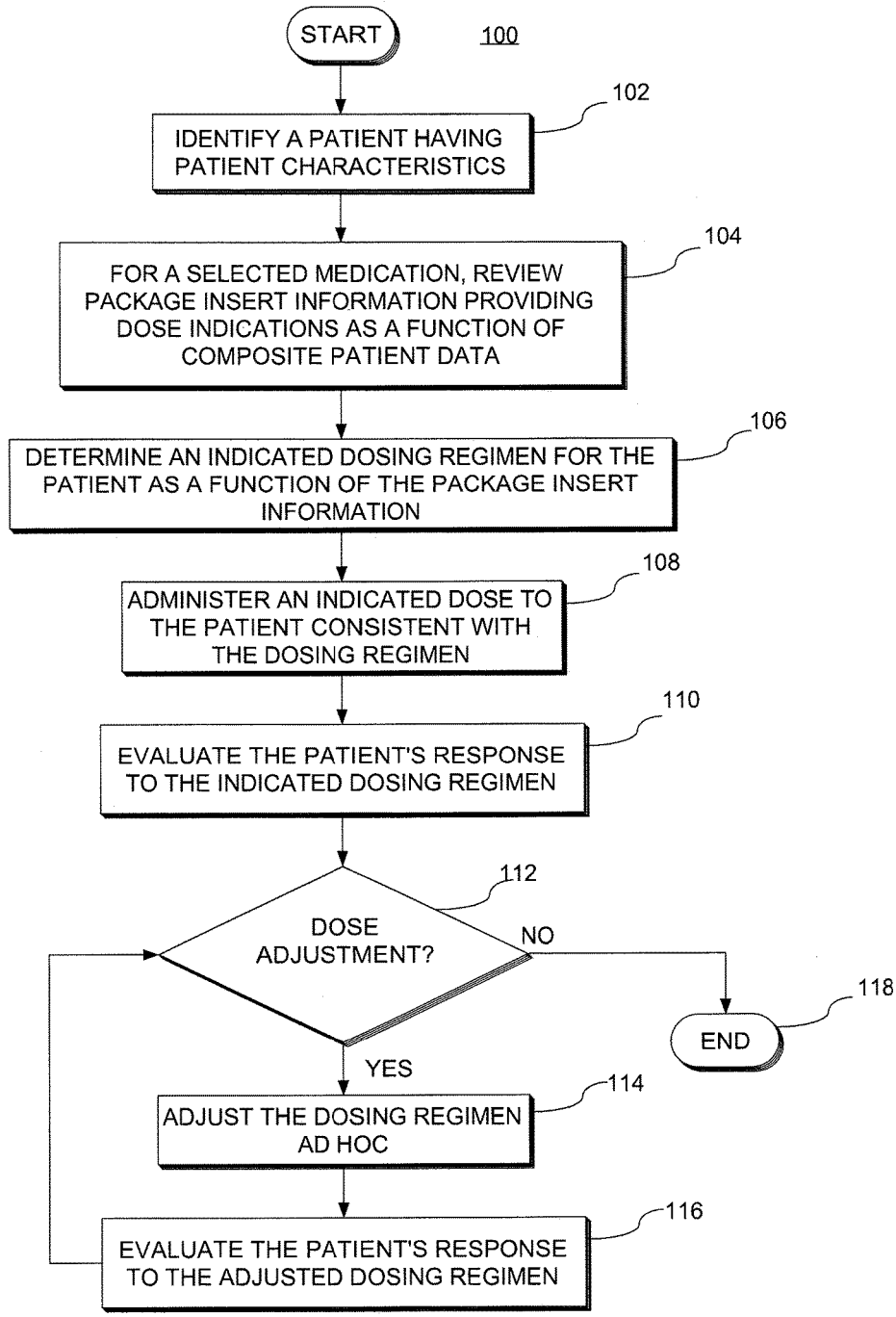
FIG. 1 is a flow diagram illustrating an exemplary prior art method for developing a medication dosing regimen for a patient.

The present invention provides a system and method for providing patient-specific medication dosing as a function of mathematical models updated to account for an observed patient response, such as a blood concentration level, or a measurement such as blood pressure or hematocrit. More specifically, the present invention provides a system and method for predicting, proposing and/or evaluating suitable medication dosing regimens for a specific individual as a function of individual-specific characteristics and observed responses of the specific individual to the medication. Conceptually, the present invention provides the prescribing physician with access, in a direct way, to mathematical models of observed patient responses to a medication when prescribing the medication to a specific patient. In prescribing an initial dose, the present invention allows for use of published mathematical model(s) to predict a specific patient's response as a function of patient-specific characteristics that are account for in the model(s) as patient factor covariates. Accordingly, the prescribing physician is able to leverage the model(s) in developing a reasonably tailored initial dose for a specific patient, as a function of the specific patient's characteristics, with much greater precision than a PI can provide.

However, the forecasting and resulting dosing regimen based on the model(s) is somewhat limited in that it is based on a hypothetical typical patient's response having the same patient characteristics. Accordingly, the forecasting and resulting dosing regimen is not likely to be optimal because the published mathematical models cannot account for the patient's uniqueness, i.e. the fact that the patient's response is likely to be unique and not typical. To account for this uniqueness, or between-subject variability (BSV), the present invention allows for further use of the specific patient's observed response to the initial dosing regimen to adjust the dosing regimen. Specifically, the inventive system and method uses the patient's observed response in conjunction with the published mathematical model(s) and patient-specific characteristics to account for BSV that cannot be accounted for by the mathematical models alone. Accordingly, the present invention allows observed responses of the specific patient to be used refine the models and related forecasts, to effectively personalize the models so that they may be used to forecast expected responses to proposed dosing regimens more accurately for a specific patient. By using the observed response data to personalize the models, the models are modified to account for between-subject variability (BSV) that is not accounted for in conventional mathematical models, which described only typical responses for a patient population, or a "typical for covariates" response for a typical patient having certain characteristics accounted for as covariates in the model.

Conceptually, the present invention allows the prescribing physician to develop a personalized dosing regimen using one or more published mathematical models reflecting actual clinical data, without the loss of resolution in the data and/or model that results from distillation of the actual clinical data into a relatively coarsely stratified set of recommendations for an "average" or "typical" patient, as in a PI.

The model-based development of such patient-specific medication dosing regimens eliminates or reduces the trial-and-error aspect of conventional dosing regimen development. Further, such model-based development shortens the length of time to develop a satisfactory or optimal dosing regimen, and thus eliminates or reduces associated waste of medications, time or other resources, as well as reduces the amount of time that a patient is at risk of undesirable outcomes.

Generally, the system and method involves gathering of mathematical models developed from clinical data gathered from patients to whom a particular medication had been administered, processing the models to create a composite model rich in patient data, and determining patient-specific dosing regimens as a function of patient-specific observed response data processed in conjunction with data from the mathematical model(s). More specifically, the system and method uses Bayesian averaging, Bayesian updating and Bayesian forecasting techniques to develop patient-specific dosing regimens as a function of not only generic mathematical models and patient-specific characteristics accounted for in the models as covariate patient factors, but also observed patient-specific responses that are not accounted for within the models themselves, and that reflect BSV that distinguishes the specific patient from the typical patient reflected by the model.

In other words, the present invention provides a system and method that takes into account variability between individual patients that is unexplained and/or unaccounted for by traditional mathematical models (e.g., patient response that would not have been predicted based solely on the dose regimen and patient factors). Further, the present invention allows patient factors accounted for by the models, such as weight, age, race, laboratory test results, etc., to be treated as continuous functions rather than as categorical (cut off) values. By doing so, the present system and method adapts known models to a specific patient, such that patient-specific forecasting and analysis can be performed, to predict, propose and/or evaluate dosing regimens that are personalized for a specific patient. Notably, the system and method can be used not only to retroactively assess a dosing regimen previously administered to the patient, but also to prospectively assess a proposed dosing regimen before administering the proposed dosing regimen to the patient, or to identify dosing regimens (administered dose, dose interval, and route of administration) for the patient that will achieve the desired outcome.

Conceptually, observed patient-specific response data is effectively used as "feedback" to adapt a generic model describing typical patient response to a patient-specific model capable of accurately forecasting patient-specific response, such that a patient-specific dosing regimen can be predicted, proposed and/or evaluated on a patient-specific basis.

Further, even before incorporating observed response data to adapt the generic model, the present invention allows for identification of an initial dosing regimen that is better than would be suggested by a PI or any one mathematical model. More specifically, in one embodiment, an initial dosing regimen is based on a composite model comprised of a plurality of patient data-rich mathematical models. In such an embodiment, the initial dosing regimen is more closely matched to a specific patient's needs than a PI's generic recommendation for an "average" patient.

By refining a particular patient's initial dosing regimen as a function of observed patient-specific data, in view of the composite mathematical model, a personalized, patient-specific dosing regimen is developed, and further is developed quickly. It will be appreciated that the exemplary method is implemented and carried out by a computerized model-based patient specific medication dosing regimen recommendation system 200 with input provided by a human operator, such as a physician, and thus acts as a recommendation engine and/or physician's expert system providing information for consideration by a prescribing physician.

Figure 2:
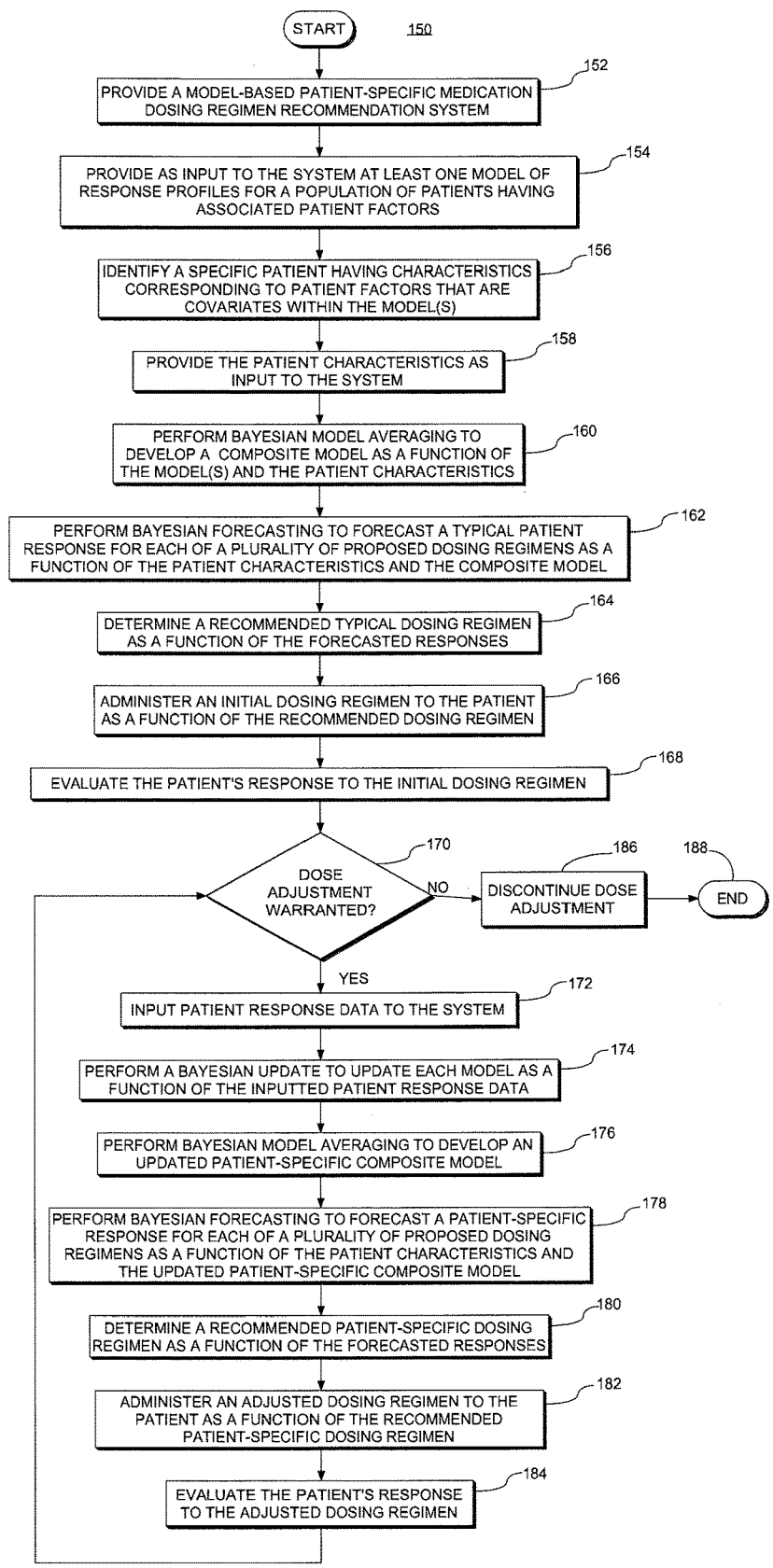
FIG. 2 is a flow diagram illustrating an exemplary method for providing patient-specific medication dosing as a function of mathematical models updated to account for an observed patient response in accordance with an exemplary embodiment of the present invention.
Figure 3:
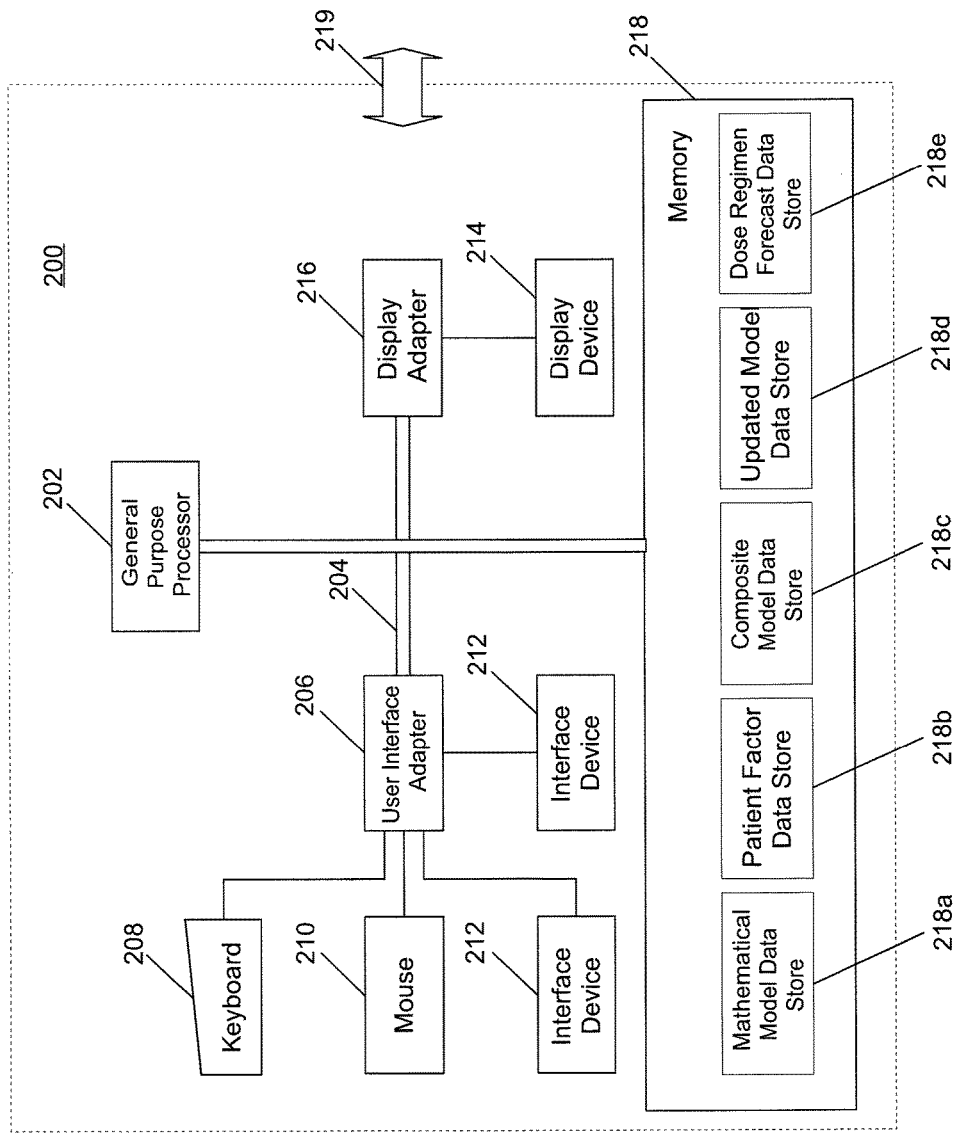
FIG. 3 is a schematic diagram of an exemplary system for providing patient-specific medication dosing as a function of mathematical models updated to account for an observed patient response in accordance with an exemplary embodiment of the present invention.

An exemplary embodiment of the present invention is discussed below with reference to FIG. 2. FIG. 2 shows a flow diagram 150 illustrating an exemplary method for providing patient-specific dosing based not only on mathematical models describing responses for a population of patients, but also on observed response data for the specific patient to be treated. Referring now to the flow diagram 150 of FIG. 2, the exemplary method begins with providing a mathematical model-based patient-specific medication dosing regimen recommendation system 200, as shown at 152. An exemplary system 200 is shown in FIG. 3 and is discussed in detail below. By way of example, the system 200 may include conventional hardware and software typical of a general purpose desktop, laptop/notebook or tablet computer. However, in accordance with the present invention, the system 200 is further specially-configured with hardware and/or software comprising microprocessor-executable instructions for specially-configuring the system 200 to carry out the method described below.

Referring again to FIG. 2, the method next involves providing at least one mathematical model to the system, as shown at 154. In one embodiment, the mathematical model is provided as part of a software module or library that is modular in nature, and that is manipulated by a software program comprising microprocessor-executable instructions for specially-configuring the system 200 to carry out the method described below. By way of example, these models may be pre-stored on the system, may be added to the system on a periodic basis, e.g., as part of distributed updates periodically stored on the system, or may be downloaded from the Internet or another network on-demand, or other electronic media. Alternatively, the mathematical model may not be part of a software module or library, but rather may be hard-coded into, or otherwise be an integral part of, a unitary software program. In either case, the model is provided as input to the system, as shown at step 154, FIG. 2, and is stored in the system's memory, e.g., in mathematical model data store 218a, FIG. 3.

Any suitable mathematical model may be used. A suitable mathematical model is a mathematical function (or set of functions) that describes the relationship between dosing regimen and observed patient exposure and/or observed patient response (collectively "response") for a specific medication. Accordingly, the mathematical model describes response profiles for a population of patients. Generally, development of a mathematical model involves developing a mathematical function/equation that defines a curve that best "fits" or describes the observed clinical data, as will be appreciated by those skilled in the art.

Typical models also describe the expected impact of specific patient characteristics on response, as well as quantify the amount of unexplained variability that cannot be accounted for solely by patient characteristics. In such models, patient characteristics are reflected as patient factor covariates within the mathematical model. Thus, the mathematical model is typically a mathematical function that describes underlying clinical data and the associated variability seen in the patient population. These mathematical functions include terms that describe the variation of an individual patient from the "average" or typical patient, allowing the model to describe or predict a variety of outcomes for a given dose and making the model not only a mathematical function, but also a statistical function, though the models and functions are referred to herein in a generic and non-limiting fashion as "mathematical" models and functions.

It will be appreciated that many suitable mathematical models already exist and are used for purposes such as drug product development. Examples of suitable mathematical models describing response profiles for a population of patients and accounting for patient factor covariates include pharmacokinetic (PK) models, pharmacodynamic (PD) models, and exposure/response models, which are well known to those of skill in the art. Such mathematical models are typically published or otherwise obtainable from medication manufacturers, the peer-reviewed literature, and the FDA or other regulatory agencies. Alternatively, suitable mathematical models may be prepared by original research.

It should be noted that in a preferred embodiment, multiple mathematical models for a single medication are provided as input to the system 200, to the extent they are available. Each mathematical model may be stored in the memory 218 of the system 200 as a mathematical function and/or in the form of a compiled library module.

Next, the method involves identifying a specific patient having patient-specific characteristics, as shown at step 156. This step may be performed by a physician or other human and may involve, for example, examination of a patient and gathering and/or measuring patient-specific factors such as sex, age, weight, race, disease stage, disease status, prior therapy, other concomitant diseases and/or other demographic and/or laboratory test result information. More specifically, this involves identifying patient characteristics that are reflected as patient factor covariates within the mathematical model(s). For example, if the model is constructed such that it describes a typical patient response as a function of weight and gender covariates, this step would include identifying the patient's weight and gender characteristics (e.g., 175 pounds, male). Any other characteristics may be identified that have been shown to be predictive of response, and thus reflected as patient factor covariates, in the mathematical models. By way of example, such patient factor covariates may include weight, gender, race, lab results, disease stage and other objective and subjective information.

Next, the method involves providing the patient-specific characteristics as input to the system 200, as shown at step 158. By way of example, this may be performed by a physician or other human operator of the system by providing input via a keyboard 208, mouse 210, or touch screen, bar code/scanner, or other interface device 212 of the system 200, as shown in FIG. 3. The patient-specific characteristics may be stored in the memory 218 of the system 200, in the form of a database record, e.g., in patient factor data store 218b of FIG. 3. Accordingly, the inputted patient characteristics can be used in conjunction with the model(s) to identify a dosing regimen closely suited to a particular patient's needs, as discussed below. More specifically, the inputted patient characteristics can be used in conjunction with the model(s) to identify a dosing regimen that is "typical for covariates," i.e., that the model(s) predict to be suitable for a typical patient having the specific patient's covariate characteristics (e.g., for a typical 175 pound male patient)—which is likely to provide a better dosing regimen than a typical PI. The use of such models to develop the "typical for covariates" dosing regimen is discussed below.

In this example, multiple different mathematical models describing patient responses for a single medication are provided as input to the system 200. Accordingly, the system next performs Bayesian model averaging to develop a composite mathematical model as a function of the mathematical models provided as input to the system, and the patient-specific characteristics that are accounted for by the model(s) as patient factor covariates, as shown at step 160. More specifically, the multiple mathematical models for a single medication are then processed by the system 200 to create a composite mathematical model for the medication using Bayesian model averaging. The composite mathematical model may be stored in the memory 218 of the system 200, e.g., in RAM or in a composite model data stored 218c, as shown in FIG. 3.

Generally, Bayesian model averaging offers a systematic method for analyzing specification uncertainty and checking the robustness of one's results to alternative model specifications. Bayesian model averaging accounts for model uncertainty which can arise from poor parameter precision, model mis-specification or other deficiencies that arise from using a single model. The standard practice of selecting a single model from some class of models and then making inferences based on this model ignores model uncertainty, which can impair predictive performance and overestimate the strength of evidence. Bayesian model averaging allows for the incorporation of model uncertainty into an inference. The basic idea of Bayesian model averaging is to make inferences based on a weighted average over a model space that includes several models. This approach accounts for model uncertainty in both predictions and parameter estimates. The resulting estimates incorporate model uncertainty and thus may better reflect the true uncertainty in the estimates. When several mathematical models have been published, the Bayesian averaging of these models produces a weighted estimate of patient response, weighted relative to the amount of data used to create the original individual models, the precision and performance of the models, and the number of models combined in the Bayesian averaging step, or alternatively weighting may be set by the user or incorporated into the system using a Markov-Chain Monte-Carlo (MCMC) approach. Thus, the development of a composite mathematical model from multiple mathematical models for a single medication compensates for limitations that may exist in any single model, and provides a more complete and robust mathematical model than is typically used in preparation of a PI.

Bayesian model averaging techniques are well known in the art. The methods implemented for Bayesian model averaging vary depending on the type of data and models being averaged, but most commonly are averaged using a Markov chain Monte Carlo model composition (MC3) method. A description of exemplary methods used for Bayesian model averaging is provided in Hoeting J A, Madigan D, Raftery A E, Volinsky C T. Bayesian Model Averaging: A Tutorial. Statistical Science 1999, 14(4)382-417, the entire disclosure of which is hereby incorporated herein by reference.

Techniques for applying Bayesian averaging to mathematical models are well-known in the art. By way of example, Bayesian averaging as a mathematical technique is well-known in the contexts of political science (see e.g., Bartels, Larry M. "Specification Uncertainty and Model Averaging." American Journal of Political Science 41:641-674; 1997), evaluation of traffic flow and accident rates (see e.g., Demirhan H Hamurkaroglu C "An Application of Bayesian Model Averaging Approach to Traffic Accidents Data Over Hierarchical Log-Linear Models" Journal of Data Science 7:497-511; 2009), and toxicology evaluations (see e.g., Morales K H, Ibrahim J G, Chen C-H Ryan L M "Bayesian Model Averaging With Applications to Benchmark Dose Estimation for Arsenic in Drinking Water" JASA 101(473):9-17, 2006).

By way of further example, Bayesian model averaging is a method of using multiple mathematical models to make predictions, as is well known, for example, in the field of weather forecasting, e.g., to predict a tropical storm's most likely path as a function of different paths predicted by different models. See, e.g., Raftery A E, Gneiting T, Balabdaoui F, and Polakowski M "Using Bayesian Model Averaging to Calibrate Forecast Ensembles" Mon. Wea. Rev., 133, 1155-1174; 2005.

Figure 7A:
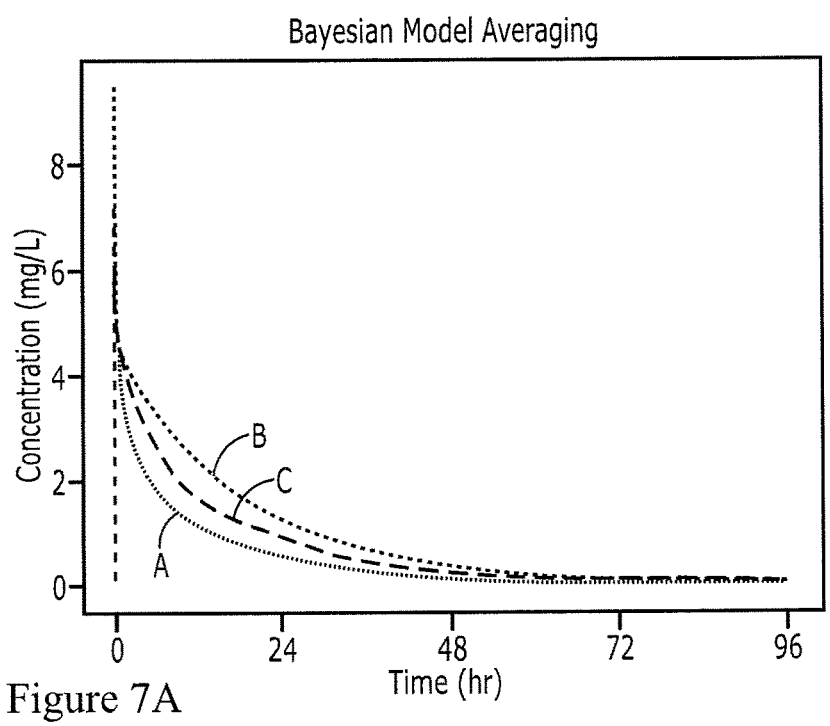
FIGS. 7A and 7B are exemplary graphs of blood level concentration as a function of time, illustrating the impacts of Bayesian model averaging and updating.

Consistent with the present invention, a Bayesian model averaging approach is used for forecasting patient response when multiple patient response models are available. An example involving Bayesian model averaging of multiple mathematical patient response models is shown in FIG. 7A. Referring now to FIG. 7A, the dashed red (A) and green (B) lines represent the expected concentration time profile from two different mathematical models. The dashed red line (A) is derived a first mathematical model as published by Xu Z, Mould D R, Hu C, Ford J, Keen M, Davis H M, Zhou H, "A Population-Based Pharmacokinetic Pooled Analysis of Infliximab in Pediatrics." The dashed green line (B) is derived from a second mathematical model as published by Fasanmade A A, Adedokun O J, Ford J, Hernandez D, Johanns J, Hu C, Davis H M, Zhou H, "Population pharmacokinetic analysis of infliximab in patients with ulcerative colitis." Eur J Clin Pharmacol. 2009; 65(12):1211-28. In this example, concentration time profiles arising from both models are utilized and a composite model (shown in a dashed blue line (C)) representing a weighted average is generated by Bayesian model averaging, as shown in FIG. 7A.

It should be noted, however, that the inventive method and system does not require multiple models as described in the example of FIG. 2. In alternative embodiments, a single model may be used in lieu of a composite model, and the corresponding Bayesian model averaging step(s) may be omitted.

It is further noted for clarity that one or more mathematical models can be provided as input to and stored in the system 200 for each of multiple medications, though in the example of FIG. 2, only a single medication is discussed for illustrative purposes.

Referring again to FIG. 2, the system 200 next performs Bayesian forecasting to forecast typical patient responses for each of a plurality of proposed dosing regimens, as shown at step 162. This step involves the system's use of Bayesian forecasting techniques to test dosing regimens for the specific patient as a function of the patient-specific characteristics accounted for as patient factor covariates within the models, and the composite mathematical model. Forecasted patient responses may be stored in the system's memory 218, e.g., in dose regimen forecast data store 218e. This forecasting, based on the composite model, involves evaluating dosing regimens based on forecasted responses for a typical patient with the patient-specific characteristics, which may be referred to as the "typical for covariates" values. Techniques for applying Bayesian forecasting to mathematical models are well-known in the art.

Generally, Bayesian forecasting involves using mathematical model parameters to forecast the likely response that a specific patient will exhibit with varying dose regimens. Notably, in this step the forecasting allows for determination of a likely patient response to a proposed dosing regimen before actual administration of a proposed dosing regimen. Accordingly, the forecasting can be used to test a plurality of different proposed dosing regimens (e.g., varying dose amount, dose interval and/or route of administration) to determine how each dosing regimen would likely impact the patient, as predicted by the patient-specific factors and/or data in the model/composite model.

In other words, this forecasting step involves use of the published models to evaluate dosing regimens to the extent that the published models are capable of evaluating dosing regimens, which is limited to analysis for a typical patient having the specific patient's patient factor covariates. While the resulting dosing regimen (corresponding to a satisfactory or best forecasted patient response) is likely more accurate than one that could be provided by a PI, it is not truly personalized for the specific patient being treated, as it does not account for unique characteristics of the patient being treated. For example, a specific 175 pound male patient may respond to a particular dosing regimen differently from a typical 175 pound male. Thus, the composite model is used to predict dosing regimens that would be expected to be suitable and/or optimal for a typical patient with the patient-specific characteristics.

More specifically, the system performs multiple forecasts of patient responses to evaluate multiple proposed dosing regimens based on the patient's characteristics, by referencing and/or processing the composite model. The system may determine each dosing regimen to be adequate or inadequate for meeting a treatment objective or target profile. For example, the target profile may involve maintenance of a trough blood concentration level above a therapeutic threshold. Further, the system may compare forecasts of patient responses to various dosing regimens, and create a set of satisfactory or best dosing regimens for achieving the treatment objective or target profile.

In one embodiment, the multiple proposed dosing regimens are provided as input to the system by the user in a manual and/or arbitrary fashion. For example, the user may provide typed input to propose a dosing regimen to be evaluated, and in response the system will perform Bayesian forecasting to forecast the patient's response to the proposed dosing regimen. The user may subsequently provide other input to propose another dosing regimen to be evaluated. For example, the dose, dose interval, and/or route of administration may be varied among the proposed dosing regimens to be evaluated. This is essentially a trial-and-error approach, albeit a sophisticated one based on continuous-function mathematical models accounting for patient factor covariates, that permits the physician to test proposed dosing regimens against the composite model.

In another embodiment, the system follows an automated search algorithm to automatedly propose and test proposed dosing regimens to optimize the dosing regimen within the range of published clinical experience. In a preferred embodiment, the optimizing algorithm uses Bayesian forecasting, but proposes doses, dose intervals and/or routes of administration systematically. Regimens that achieve the desired goal are marked as feasible and stored by the system. The resulting output is a series of possible initial dosing regimens that are expected to achieve the desired clinical outcome, as predicted by the composite mathematical model and the patient factor covariates.

Figure 4:
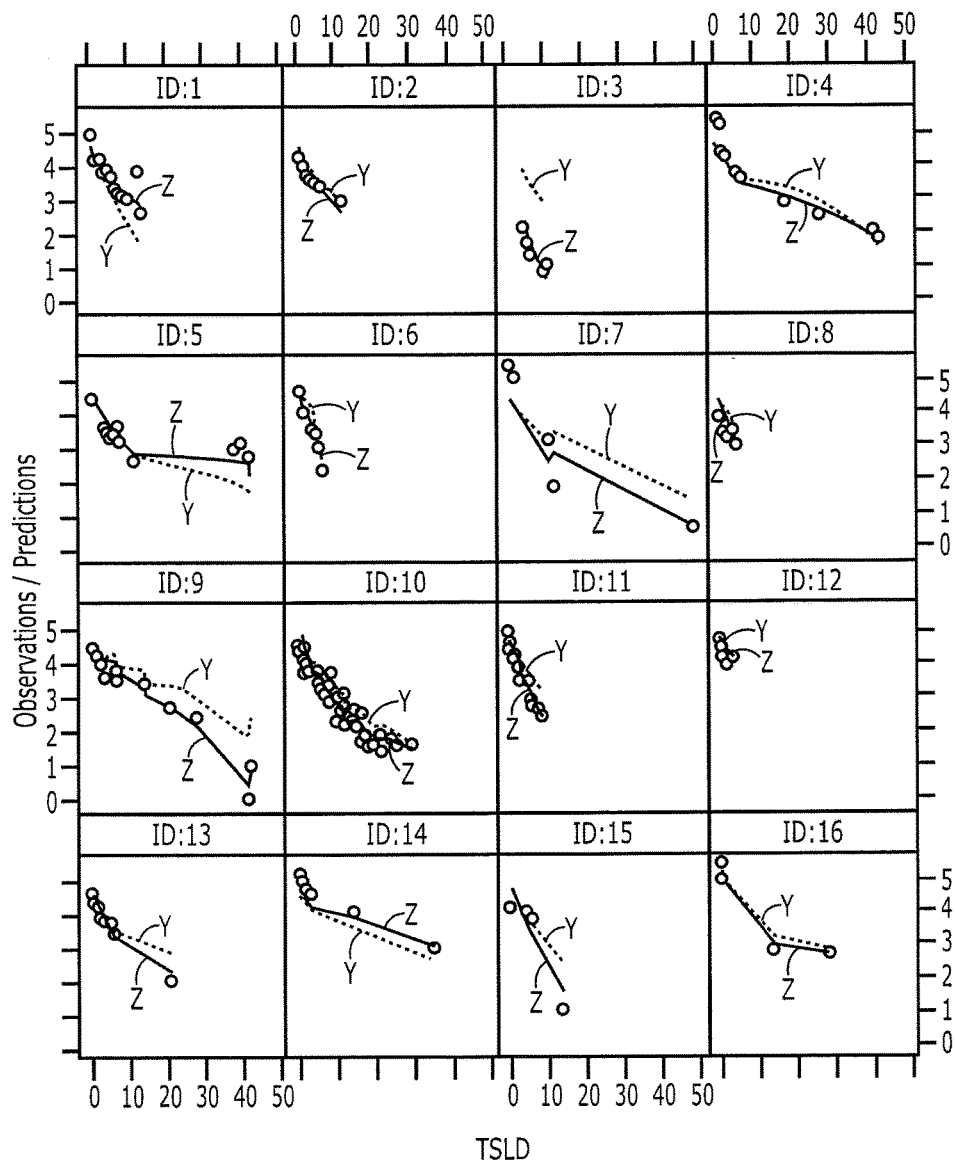
FIG. 4 is a series of graphs showing relationships between times since last dose (TSLD) and observed/predicted patient responses for sixteen exemplary patients.

An illustrative example is provided below with reference to FIG. 4. Referring now to FIG. 4, patient response for each of 16 different patients (ID:1-ID:16) is shown as a function of time since the last dose (TSLD, hours). More specifically, the blue line (Y) is developed using the above-reference published mathematical model for infliximab (Xu et al). More specifically, each blue line (Y) is a plot of the average ("typical") expected patient response predicted using the mathematical model and the patient-specific factors (such as weight) that are provided as covariates within the published model. Accordingly, this blue line (Y) represents clinical data compiled for a plurality of patients, and is thus somewhat of an "average" or "typical" representation. Thus it can be seen in FIG. 4 that some individual patient responses (open circle symbols) are higher than the blue line (as for ID:1 and ID:5) and other individual patient responses are lower than the blue line (as for ID:3, ID:7, and ID:9).

Therefore, the blue line ("typical for covariates") recommendations are likely better than a dosing indication in a PI, which often does not take in account patient factors, or all of the important patient factors, or may be based upon a coarse stratification of expected patient response. However, the blue line (Y) does not necessarily provide an optimal dosing regimen for a specific patient because it does not take into account the variability in response seen between patients with the same patient factors, sometimes referred to as the between-subject variability, or "BSV." Thus, two patients with the same patient factors may have different observed responses to a particular dose of a therapeutic drug as a result of variability that is not explained by individual patient factors in the published model(s).

In accordance with the teachings herein, the inventive system would forecast patient responses for proposed dosing regimen(s) (FIG. 2 Step 162) based on the blue line (Y)

shown in FIG. 4. Specifically for ID:3 in FIG. 4, the initial dosing regimen provided by the system, based only on patient factors (covariates), would be expected to produce a response reflective of the blue line.

Referring again to FIG. 4, the red lines (Z), discussed below, are developed in accordance with the teachings of the present invention to account not only for patient-specific factors that are covariates within the model, but also for observed patient-specific responses consistent with the present invention. More specifically, the red lines (Z) are based upon mathematical models that have been Bayesian updated to reflect observed patient-specific responses. Thus, the red lines (Z) are likely more representative of the proper dosing for the specific patient being treated. In accordance with the present invention, as discussed in further detail below, subsequent dosing regimen recommendations (using Bayesian forecasting) for ID:3 would be based on the Bayesian updated composite model (e.g. the solid blue line (D) in FIG. 7B or the red line Z in FIG. 4) that accounts for the observed patient data (e.g. the open circles), as discussed below.

Accordingly, in the example of FIG. 4, the blue (Y) and red (Z) lines predicted as patient responses for each patient ID:1-ID:16 are different, based on the patient-specific factors that are covariates within the model and the observed patient-response data.

After performing one or more Bayesian forecasts to provide one or more forecasted typical patient responses, the physician and/or the system may compare the various forecasted, so that an appropriate dosing regimen may be identified.

Referring again to FIG. 2, the exemplary method next involves the system determining a recommended typical dosing regimen as a function of the forecasted responses, as shown at step 164. For example, the recommended typical dosing regimen may be selected by the system 200 as one of a plurality of Bayesian forecasts that were tested for achieving a treatment objective, based on feasibility and practicability, etc. For example, the recommended typical dosing regimen may be selected as the one of several tested/forecasted proposed dosing regimens that were identified as being able to maintain an exposure (i.e., drug concentration) above a therapeutic level. For example, in FIGS. 10B-10F, for the "Difficult Patient", multiple dose intervals were tested using Bayesian forecasting. As will be appreciated from FIGS. 10B-10F, the forecasting shows that dosing regimens including dose intervals of 1, 2 and 4 weeks can maintain drug concentrations at a target level (represented by black dashed lines).

In one exemplary embodiment, the system 200 displays a list of recommended typical dosing regimens to a physician via its display device 214, or causes the list of recommended dosing regimens to be printed via an associated printer, or transmitted by electronic data transmission via link 219 to a mobile computing device of the physician, a computing system of a pharmacy, hospital, clinic, patient, etc. For example, a selected subset of the testing dosing regimens (e.g., top 3, top 10, etc.) may be outputted by the system to the user as recommended or suggested dosing regimens. It will be appreciated by those skilled in the art that characteristics of the "best" dosing regimen will vary according to medication characteristics and/or treatment objectives. Accordingly, in the example of FIGS. 10B-10F, the dosing regimens for the "Difficult patient" that were identified as being expected to maintain concentrations (filled circles) above the target concentration (dashed lines) (i.e. the 1, 2, and 4 week dose interval) would be displayed, printed or transmitted as the recommended typical dosing regimen(s) of step 164.

In this exemplary embodiment, the physician may then browse the recommended typical dosing regimen(s) provided as output by the system, and then determine an initial dosing regimen for administration to the patient. In doing so, the physician may select a dosing regimen from the list, or may modify a recommended dosing regimen, in accordance with the physician's judgment.

Various considerations may be taken into consideration by the physician and/or the system in determining recommended dosing regimens and/or initial dosing regimens. For example, a primary consideration may be meeting a specific treatment objective, such as maintaining a minimum blood level concentration, maintaining a target blood pressure, etc. However, other considerations may also be taken into consideration, such as ease of compliance, scheduling consideration, medication/treatment cost, etc. The system may include utility functions for taking such other considerations into account when determining the recommended typical dosing regimen(s).

The physician then directly or indirectly administers the initial dosing regimen, as shown at step 166. As compared with the techniques of the prior art discussed above with reference to FIG. 1, this initial dosing regimen is better-personalized to the specific patient to which it is administered because it is based upon an interpretation of the underlying composite mathematical and statistical model(s) as a function of the patient's personal characteristics. In other words, the initial dosing regimen is reflective of a typical-for-covariates dosing regimen determined by the model, and thus is suitable for a typical patient having the specific patient's characteristics. Accordingly, the initial dosing regimen is not based merely on a coarse interpretation of the underlying model data as reflected in generic PI dosing information. Further, it is based upon forecasted outcomes following evaluations of various doses, dose intervals and routes of administration, as part of the Bayesian forecasting process, and as a function of patient characteristics captured as patient factor covariates in a single model, or in a composite model produced by Bayesian model averaging of multiple mathematical models.

After an initial period, the physician in this exemplary method follows-up with the patient and evaluates the patient's response to the initial dosing regimen and determines whether a dose adjustment is warranted, e.g., because the patient response is deficient, as shown at steps 168 and 170. These steps may be performed in a conventional manner, as discussed above with reference to FIG. 1. Accordingly, for example, this may involve obtaining laboratory test results reflecting a patient's response to the administered dosing regimen, examining the patient, and/or asking how the patient feels.

In this exemplary embodiment, if it is determined that a dose adjustment is not warranted at 170, then dose adjustment is discontinued and the method ends, as shown at 170, 186 and 188.

However, if it is determined that a dose adjustment is warranted at 170, then patient response data resulting from the evaluation is provided as input to the system 200, as shown at 170 and 172. For example, such inputting may include inputting quantitative and/or qualitative lab result test data and/or physician assessments into the system 200. In addition, patient characteristics which may have changed may also be evaluated and/or provided as input to the system. In particular, this step involves inputting updated observed measurements patient response and updated patient-specific characteristics obtained from the specific patient.

Optionally, the system may be configured such that if a key individualized model parameter is more than ±3 standard deviations away from the key typical parameter value, the system will indicate that further use of this therapeutic drug in this patient may not be warranted, because the specific patient's response suggests that the patient will not respond sufficiently to the proposed treatment.

Referring again to FIG. 2, the system 200 next performs a Bayesian update to each of the underlying mathematical models, to update each model as a function of the inputted patient-specific characteristics (tracked as patient factor covariates within the models) based on the inputted patient response data, as shown at step 174. Preferably, this step is performed using iterative Bayesian updating, and is further performed immediately prior to the development and/or administration of the next dosing regimen. This updating with observed patient-specific data takes into account the specific patient's observed response, and thus updates the model(s) to account for between subject variability (BSV) that is not accounted for in the models themselves. Accordingly, the application of Bayesian updating allows the software to account for changing patient condition or patient factors, thus implicitly correcting the dosing regimen forecasts and recommendations.

Techniques for applying Bayesian updating to mathematical models are well-known in the art. See, e.g., Duffull S B, Kirkpatrick C M J, and Begg E J Comparison of two Bayesian approaches to dose-individualization for once-daily aminoglycoside regimens Br J Clin Pharmacol. 1997; 43(2): 125-135.

Generally, Bayesian updating involves a Bayesian inference, which is a method in which Bayes' rule is used to update the probability estimate for a hypothesis as additional evidence is obtained. Bayesian updating is especially important in the dynamic analysis of data collected over time (sequentially). The method as applied here uses models that describe not only the time course of exposure and/or response, but also include terms describing the unexplained (random) variability of exposure and response. It involves applying a "prior" to form the underlying hypothesis. The "prior distribution" is the distribution of the parameter(s) before any data are observed. In our example, the prior distribution is the underlying series of mathematical models describing the expected exposure and/or response following administration of a medication without the influence of observed individual patient data. In our example, this would be the initial estimates generated for the initial dosing regimen. The "sampling distribution" is the distribution of the observed data conditional on its parameters. This is also termed the "likelihood," especially when viewed as a function of the parameter(s) and is the observed response data. The marginal likelihood (sometimes also termed the evidence or the "posterior") is the distribution of the observed data marginalized over the parameter(s). In our example, this would be the models after being updated by the input observed response data. Thus, Bayes' rule can be applied iteratively. That is, after inputting the observing response data, the resulting posterior probability can then be treated as a prior probability for the next observed response, and a new posterior probability computed from new evidence. This procedure is termed "Bayesian updating." The result of Bayesian updating is a set of parameters conditional to the observed data. The process involves sampling parameters from the prior distribution (in our example, this is all of the underlying models) and calculating the expected responses based on the underlying models. For each underlying model, the difference between the model expectation and the observed data is compared. This difference is referred to as the "objective function." The parameters are then adjusted based on the objective function and the new parameters are tested against the observed data by comparing the difference between the new model expectation and the observed data. This process runs iteratively until the objective function is as low as possible (minimizing the objective function) suggesting that the parameters are the best to describe the current data. All underlying models are thus subjected to Bayesian updating. Once all models have been updated, Bayesian averaging is conducted and a new composite model is produced.

In order to ensure that a global minimum of the objective function has been obtained, the method may involve use of a random function to interjects some variation in the process to ensure the objective function surface is adequately explored and that a true global minimum (and not a local minimum which would not reflect the best description of the observed patient response data) has been achieved. The use of a random function to ensure that a model achieves a true global minimum is well-known in the field of stochastic approximation expectation methods. However, it is believed that the use of such a random function is novel in the context of Bayesian updating.

For illustrative purposes, an example involving iterative Bayesian updating is discussed below with reference to FIGS. 6A-6D for a simple exemplary model involving three parameters (CL, V and σ). Referring now to FIGS. 6A-6D, the numbers below each Figure represent the likelihood (li) of the parameters where the likelihood is the probability of the observed data ($y_{ij}$) given the selected model parameters ($\theta_i$, $\sigma_i$) at each iteration $\{li=P(y_{ij}|\theta_i,\sigma_i)\}$. In the iterative process, the system initially tests the prior (typical) parameter values ($CL_1$, $V_1$ and $\sigma_1$, FIG. 6A) and calculates the function using these parameter values. The system then compares the calculated value (curved line) to the observed data (filled circles) and computes the likelihood (e.g., shown below FIG. 6A). The system then selects a different set of parameters from a specified prior distribution to test ($CL_2$, $V_2$ and $\sigma_2$, FIG. 6B) and again calculates the function using the second set of parameters. If the agreement between the observed data (filled circles) and predicted value (curved line) is better (e.g. the likelihood is larger) then the software will select a third set of parameters following the same trend as was used for the selection of the second set of parameters. So if the second set of parameters was smaller than the first set of parameters, the third set of parameters will be still smaller (lower) in value. If the agreement between the observed data and predicted function is worse (e.g. the likelihood is smaller), the system will automatically select a different path, in this case picking new estimates that are larger than the second parameters but smaller than the first parameters. This process repeats iteratively until the system cannot further improve the agreement between observed and predicted values ($CL_4$, $V_4$ and $\sigma_4$, FIG. 6D). It should be noted that not all parameters necessarily trend in the same way—some parameter values may be larger than the initial values and some parameter values may be smaller.

Referring again to FIG. 2, the system 200 next performs Bayesian model averaging to develop an updated patient-specific composite model from the updated underlying models, as shown at step 176. This Bayesian averaging process is similar to that described above with reference to step 160, although the Bayesian averaging in this step 176 is performed on the underlying updated models that were updated based on observed patient responses. The Bayesian averaging in step 176 produces an updated composite model. By way of example, the updated model may be stored by the system in memory 218, such as in updated model data store 218*d*. At this point, the updated patient-specific composite model parameters obtained are reflective of the observed response of the specific patient being treated, and thus more accurately reflects the individual patient, and incorporates variation as to response that is not explained by patient factors, such as age and weight. Thus, the updated patient-specific composite model better represents the expected patient response to subsequent doses.

Figure 7B:
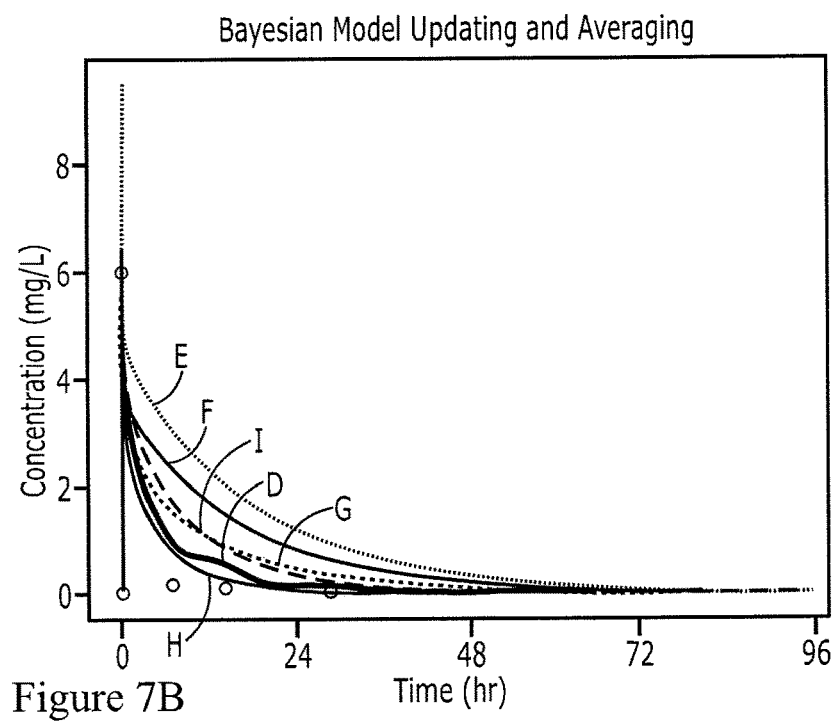

This is reflected in the examples of FIGS. 4 and 7. Referring again to FIG. 4, after administration of the initial dose to ID:3 and obtaining observed responses from patient ID:3, the individual patient response (open circles) would be shown to have deviated from the average expected response (blue line, Y). The model(s) for ID:3 would then be updated (using Bayesian updating) based on the observed response for patient ID:3 and combined into a composite model (using Bayesian averaging). In FIG. 7B, the result of Bayesian updating and Bayesian model averaging is shown. The dashed green line (E) is the Fasanmade model before Bayesian updating, the solid green line (F) is the Fasanmade model after Bayesian updating, the dashed red line (G) is the Xu model before Bayesian updating, the solid red line (H) is the Xu model after Bayesian updating, the dashed blue line (I) is the Bayesian averaged model before Bayesian updating, the solid blue line (D) is the Bayesian averaged model after Bayesian updating, and the open circles are the observed data after the administration of the initial dosing regimen. As can be seen in these figures, the solid blue line (D, updated composite model) is reflective of the observed data (open circles). Thus, it is the updated composite model reflected in the solid blue line (D) that is used for the next prediction of a dosing regimen in accordance with the present invention.

Referring again to FIG. 2, the system 200 next performs Bayesian forecasting to forecast a patient-specific response for each of a plurality of proposed dosing regimens, as shown at 178. This forecasting is performed as a function of the patient characteristics and the patient-specific composite model, which reflects observed patient-specific response data. This generally involves the same process as described above with reference to step 162, although the updated composite model is used in step 178. By way of example, this may involve using Bayesian forecasting to test a plurality of proposed doses to predict patient response for each of the proposed doses, prior to administration of the proposed doses to the patient. More specifically, such Bayesian forecasting uses the updated composite model to predict patient response for each proposed dosing regimen.

Next, the system 200 determines a recommended patient-specific dosing regimen as a function of the forecasted patient responses, as shown at step 180 of FIG. 2. Similar to the method described above with reference to step 164, the process of determining the recommended patient-specific dosing regimen may involve a manual Bayesian forecasting process in which the system receives a proposed dosing regimen provided as input by a user and projects the associated expected response, or alternatively may involve an automated search algorithm that automatedly selects and tests proposed dosing regimens to optimize the dosing regimen within the range of published clinical experience, by evaluating dose, dose interval and route of administration in view of commercially available products. For example, a list of recommended proposed patient-specific dosing regimens may be selected by the system from a plurality of Bayesian forecasts that were tested for achieving a pre-specified clinical target (in the examples of FIGS. 8 and 9, a specific target trough concentration). By way of further example, the treatment objective may be predefined for each medication and may be stored by the system. For example, the treatment objective may be to maintain a blood level concentration above a predefined therapeutic threshold.

Next, the physician reviews the recommended patient-specific dosing regimen information obtained from the system 200 and determines an adjusted patient-specific dosing regimen as a function of the forecasted responses. This may involve reviewing the system's comparison of multiple forecasted responses and selecting or modifying one of the recommend patient-specific dosing regimens as an adjusted dosing regimen.

Figure 8A:
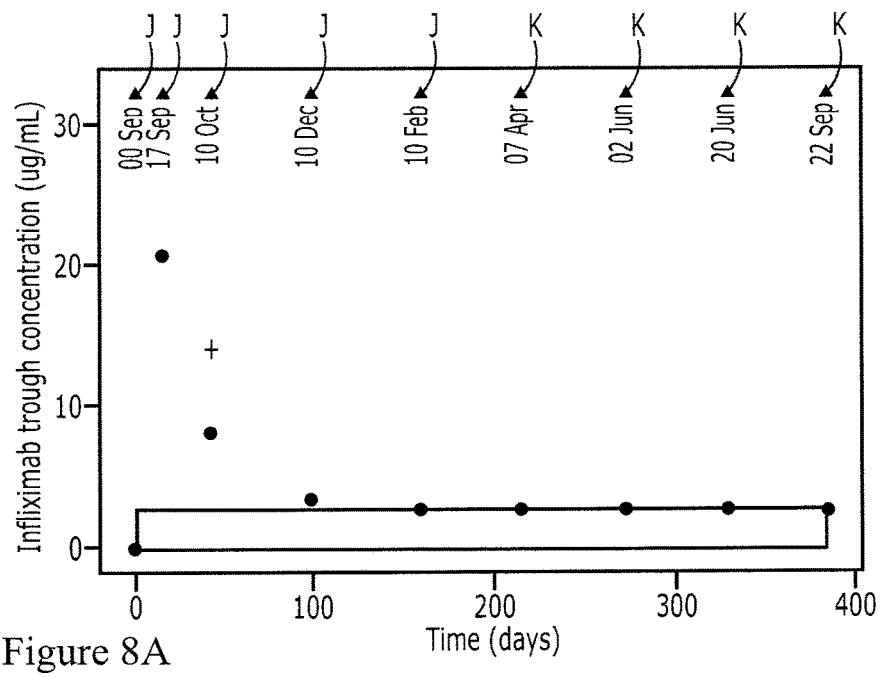
FIGS. 8A-8D and FIGS. 9A-9E are exemplary graphs showing infliximab blood level concentrations as a function of time.

The impact of Bayesian forecasting as a tool to prospectively evaluate dosing regimens is discussed below for illustrative purposes with reference to FIGS. 8A-8D. FIGS. 8A-8D show dosing regimen adjustments in a patient with moderate disease, in which all other relevant patient factors are average (the "population patient," or "typical" patient for whom the package insert drug labeling was based on). In these Figures, the shaded region is the target concentration, and the filled circles are the individual forecasted concentrations. Accordingly, the observed data are fit using the models (in this example, the Fasanmade et al. and the Xu et al. models), the models are Bayesian updated, are then averaged (using Bayesian averaging) and the resulting composite model is used to forecast expected patient response troughs (a critical consideration for therapeutic benefit in this example) for that patient for each proposed dosing regimen. The crosses are the forecasted concentrations predicted based only on patient factors (typical predicted concentrations) (i.e., predicted by the model without Bayesian updating and only as a function of model covariates), the red triangles J are actual administered doses, and the aqua triangles K are the forecast doses. FIG. 8A reflects the predicted trough concentrations achieved with a proposed labeled dose (5 mg/kg every 8 weeks), as predicted using Bayesian forecasting in step 176. It can be seen that for this patient with moderate disease, the labeled concentration does not maintain the concentrations above the target.

Figure 8B:
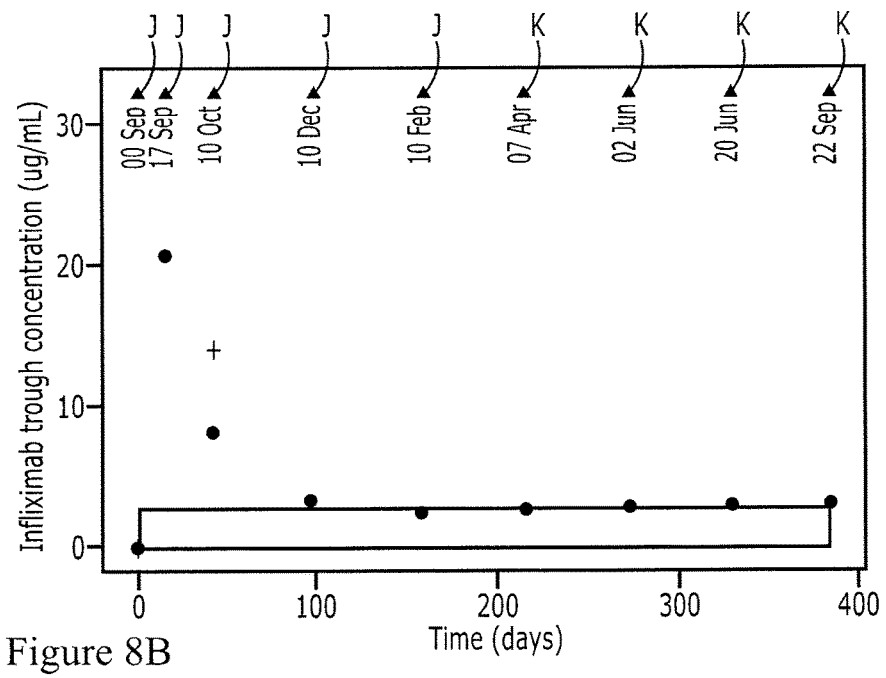

Referring now to FIG. 8B, a proposed dosing regimen of 6 mg/kg given every 8 weeks is tested as part of step 176, which provides concentrations that are at the target level and might reflect the second attempt a physician would try for a patient if they failed to respond to initial therapy.

Figure 8C:
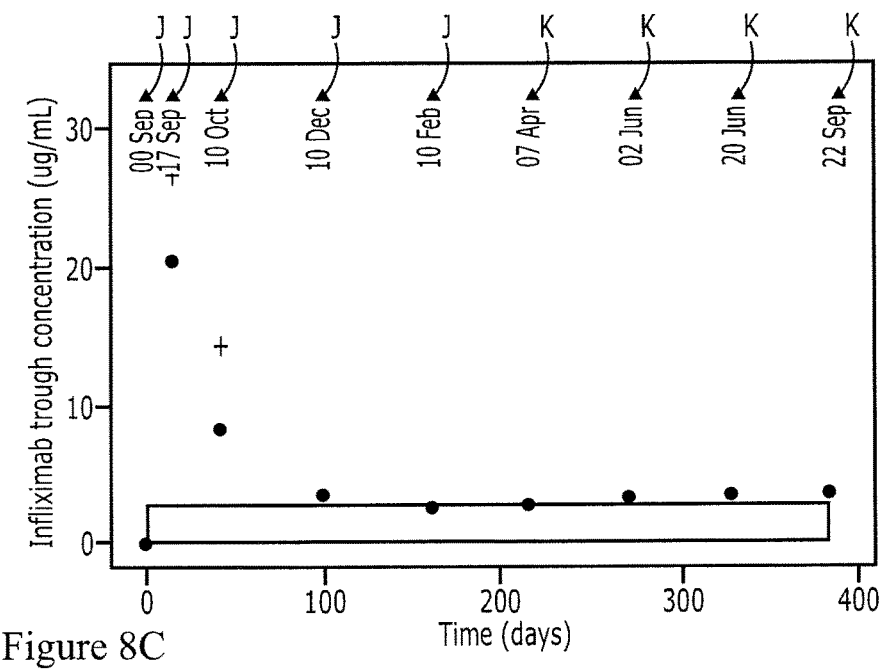
Figure 8D:
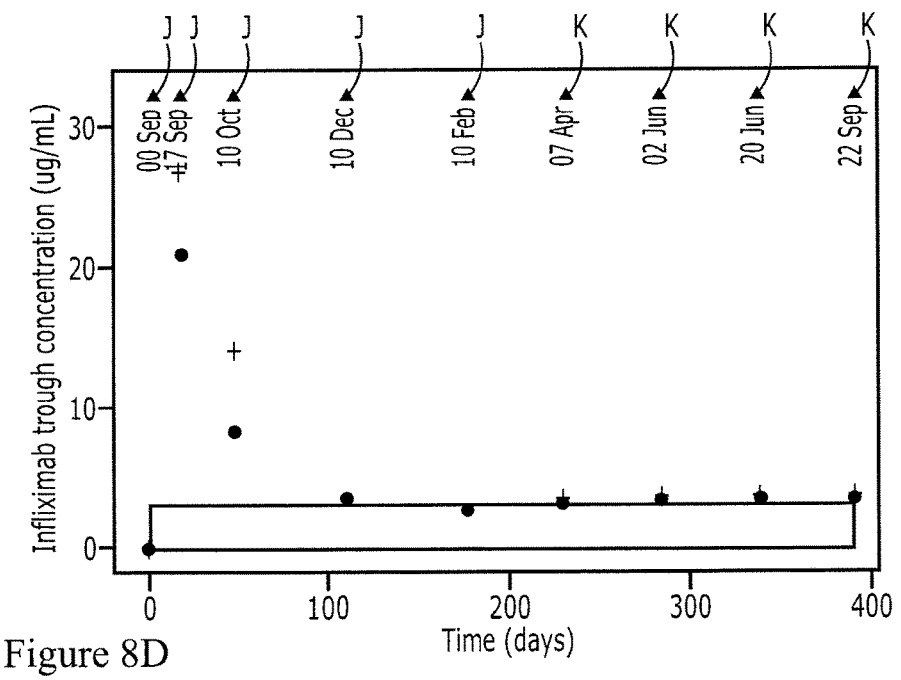

Referring now to FIG. 8C, a proposed dosing regimen of 7 mg/kg given every 8 weeks is tested as part of step 176. As noted from FIG. 8C, this proposed dosing regimen is forecasted to provide concentrations that are appropriately higher than the target concentration and might reflect the doses tried for a third attempt at dosing this patient. Referring now to FIG. 8D, a proposed dosing regimen of 5 mg/kg dose given every 7 weeks is tested and the forecast result is shown in FIG. 8D to provide adequate concentrations.

For the example of FIGS. 8A-8D, it may be noted that over a treatment interval of 56 weeks, the 7 mg/kg dose given every 8 weeks (FIG. 8C) would utilize a total dose of 49 mg/kg whereas the 5 mg/kg dose given every 7 weeks would utilize a total dose of 40 mg/kg (FIG. 8D) while providing satisfactory results (namely maintaining a minimum concentration), a 20% reduction in total administered dose, reflecting an added savings to the patient in cost and a higher margin of safety due to the overall reduction in drug exposure. Accordingly, step 178 may involve selection of the dosing regimen associated with FIG. 8D.

Figure 5A:
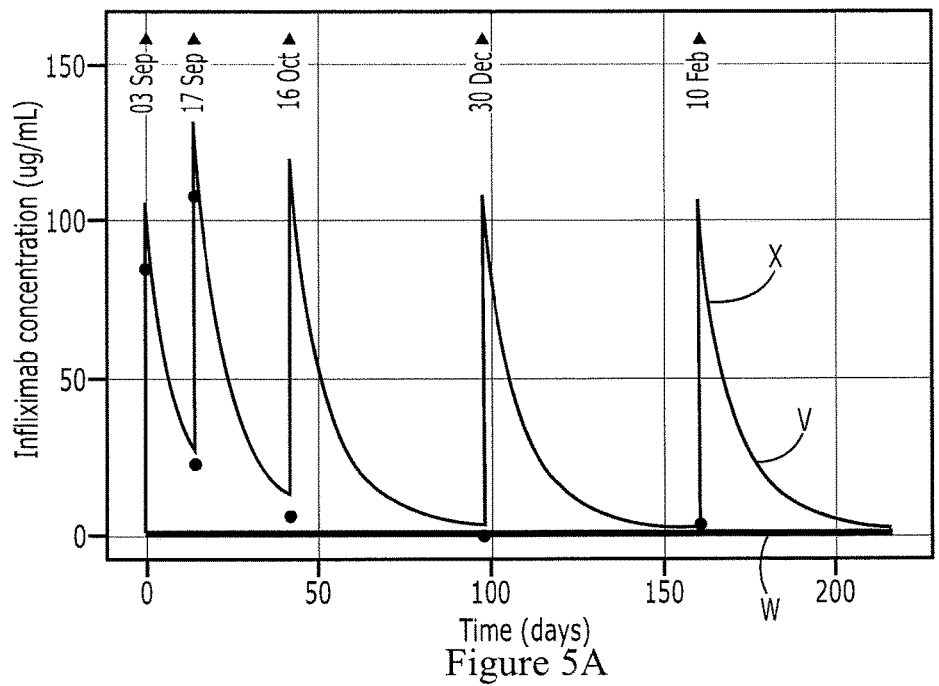
FIGS. 5A-5D are exemplary graphs showing infliximab blood level concentrations as a function of time.
Figure 5B:
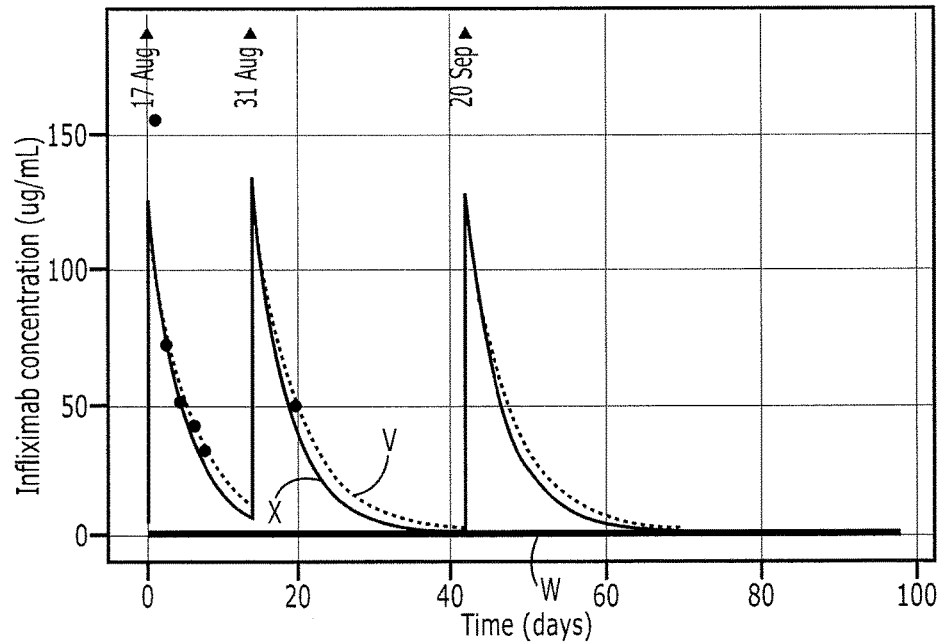
Figure 5C:
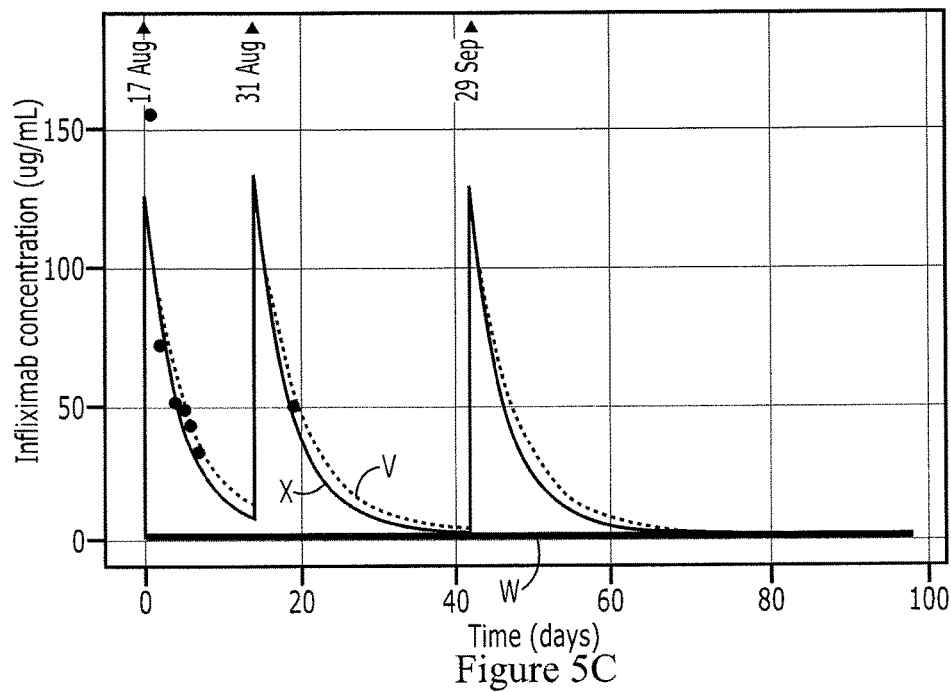
Figure 5D:
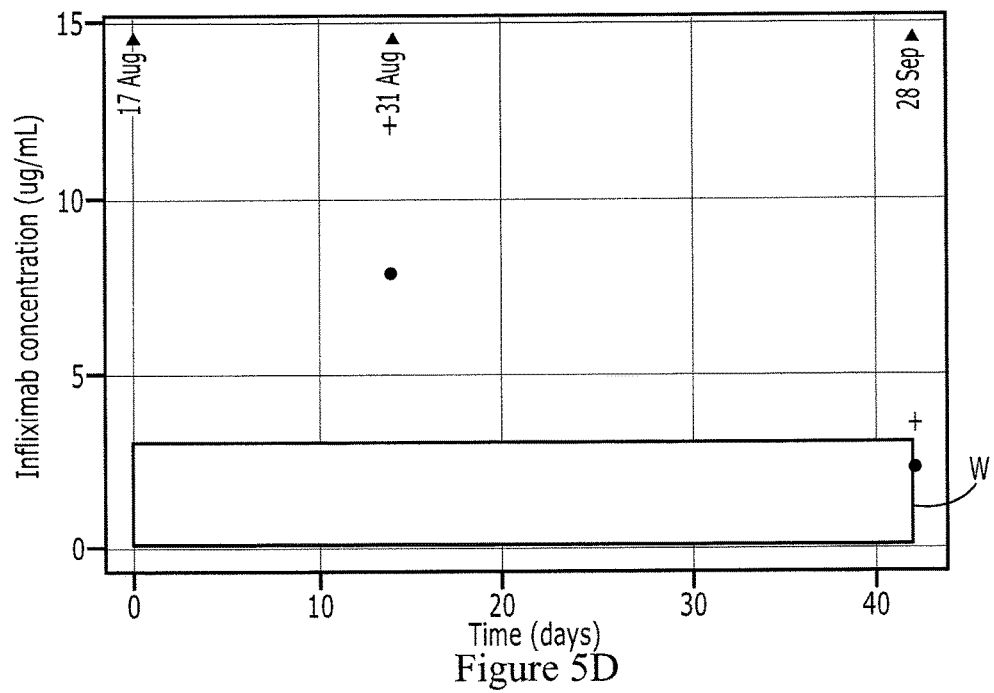
Figure 6A:
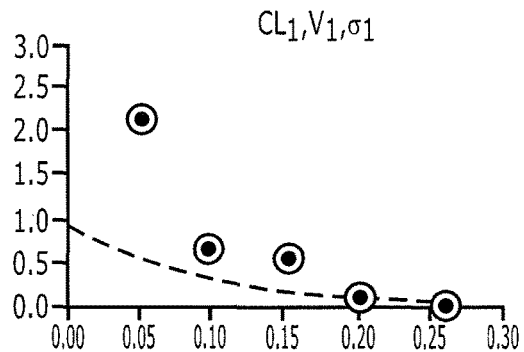
FIGS. 6A-6D are exemplary graphs illustrating an iterative Bayesian updating process.
Figure 6B:
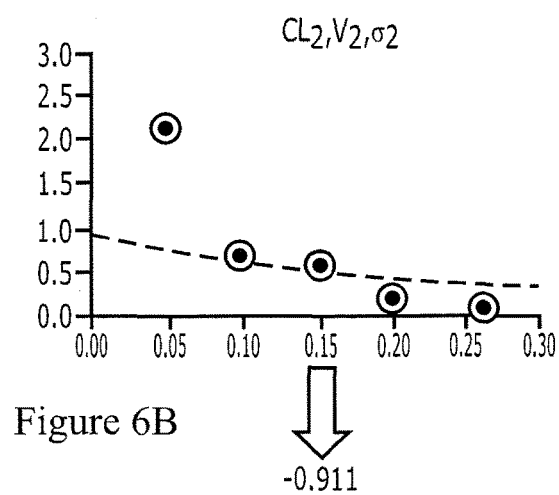
Figure 6C:
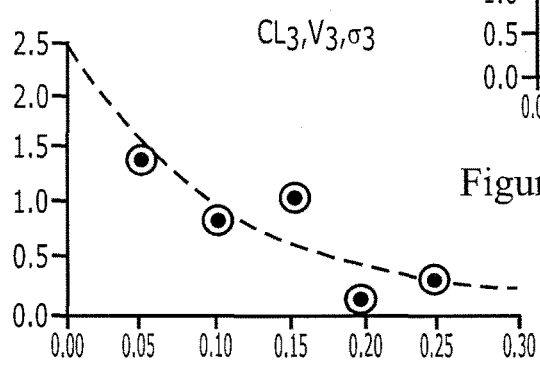
Figure 6D:
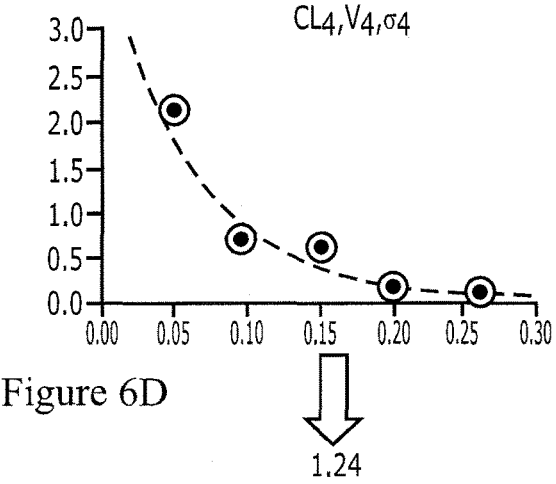

Another illustrative example is described below with reference to FIGS. 5A-5D. Referring now to FIGS. 5A-5D, the filled circles represent observed blood level concentrations as the result of lab tests, etc., the red line (W) is the target concentration as determined in this case by peer reviewed publications and current clinical practice, and the solid line (X) is the individual predicted concentration using the updated composite model, as determined by the mathematical models as updated in step 174 and as averaged in step 176, and the dashed line (V) is the typical predicted concentration (which is calculated given only covariate information without any updating, similar in concept to the blue line shown in FIG. 4, and referenced in FIG. 2 at step 160). FIGS. 5A and 5B represent data from a patient with moderate disease (a "Population" or "Typical" patient), and FIGS. 5C and 5D represent data from a patient with severe disease (a "Difficult patient").

In FIG. 5A, the solid and dashed lines X, V are superimposed because Bayesian updating has not yet been done. In FIG. 5B, Bayesian updating has been completed and the updated combined model is now based on covariates and on observed patient responses, as discussed above. Therefore, there is a difference between the typical-for-covariates concentration arising from the combined model with only patient factor information, and the patient-specific predicted concentration arising from the updated composite based on patient factor information and observed patient-specific patient-response data (i.e. the model has undergone Bayesian updating in addition to Bayesian averaging).

Referring now to FIG. 5C, the difference between the observed (filled circle) and typical predicted values (solid line, X) is more pronounced because of the severe disease. In FIG. 5D, the shaded region W is the target concentration, the filled circles are the patient-specific predicted concentrations that are predicted by the Bayesian updated model, the crosses are the concentrations predicted based only on patient factors (typical predicted concentrations and are thus based only on covariates within the model, and not as the result of Bayesian updating), and the triangles are the actual administered doses.

In FIGS. 5C and 5D, it can be seen that the patient-specific predicted concentrations taken just prior to dosing (i.e. trough concentrations, which is the metric for dosing in this example) are falling below the target concentration W that must be achieved for clinical response, as best shown in FIG. 5D. It should be noted that the typical-for-covariates ("average") predicted concentrations (crosses, based on a forecast made without Bayesian updating) suggest that the concentrations arising from the dose being evaluated should be appropriate in that the crosses are above the target level (red band) and the typical concentration are higher than the red line W, as shown in FIG. 5D. However, following Bayesian updating (filled circles, FIG. 5D) of the model to update the models to account for patient-specific response data and between subject variability, the model shows that that the dose being evaluated is not appropriate as the blue dots are below the target concentration (red band, W), and thus the target response/treatment objective will not be met.

Figure 9A:
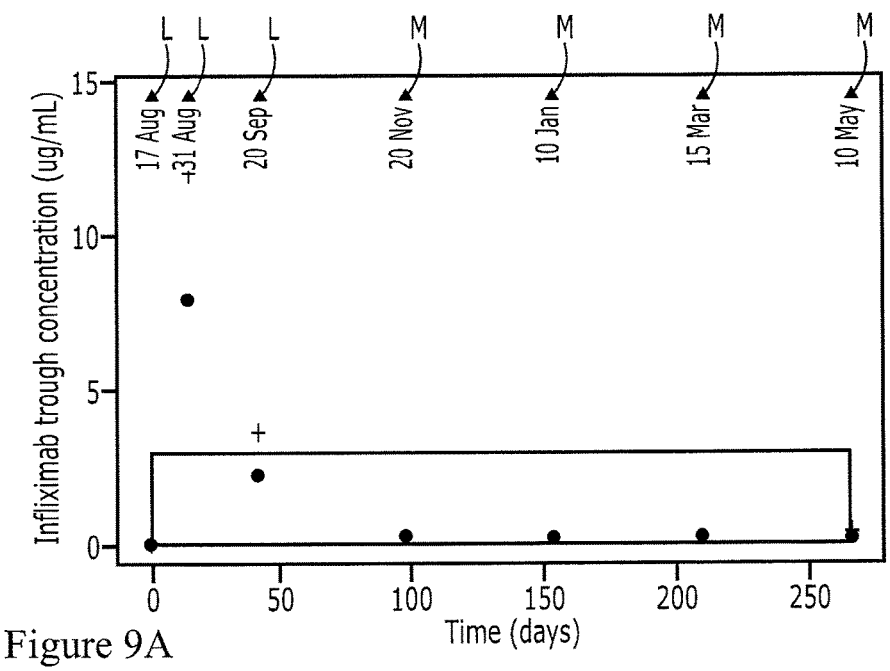
Figure 9B:
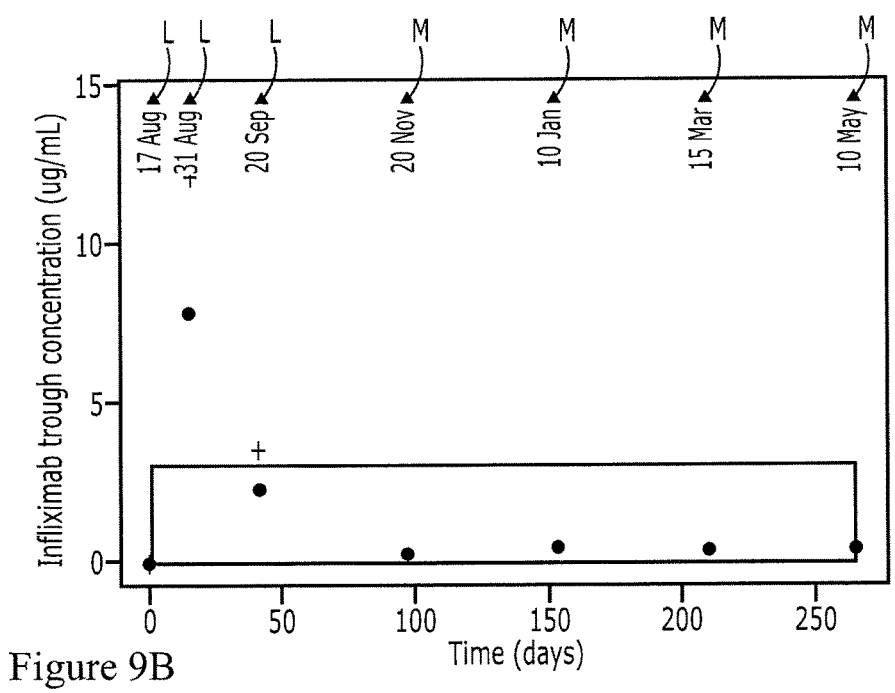
Figure 9C:
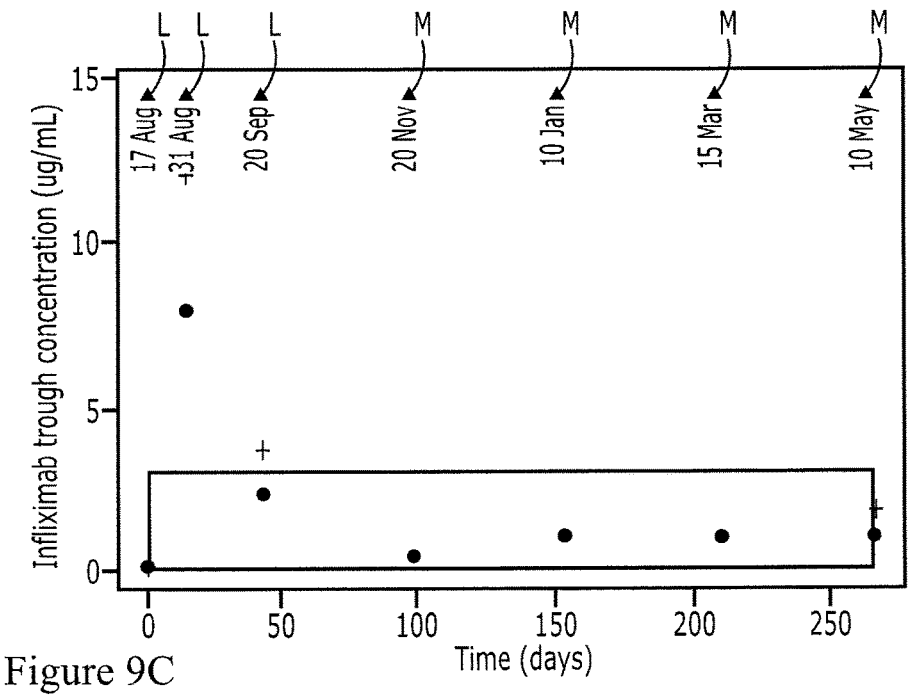

Additional examples of evaluating dose regimens are discussed below with reference to FIGS. 9A-E. Referring now to FIGS. 9A-9C, the figures represent a dose adjustment in a patient with severe disease (a "Difficult Patient" who deviates substantially from the typical "Population Patient" shown earlier). In the these Figures, the shaded region is the target concentration, the filled circles are the individual predicted concentrations (based on the Bayesian updated composite model), the crosses are the concentrations predicted based only on patient factors (typical predicted concentrations as reflected by the models, accounting for patent factors—i.e., the typical with covariates), the red triangles L are actual administered doses, the aqua triangles M are the forecast doses (i.e., Bayesian forecasted results based on the composite model, accounting for patient factors, and updated to reflect observed patient response/exposure data). FIG. 9A reflects the trough concentrations achieved with the labeled dose (5 mg/kg every 8 weeks). It can be seen that for this patient with severe disease, the labeled dose does not maintain the concentrations above the target, so a physician considering whether to prescribe this dosing regimen would likely reject it, and try to find a dosing regimen forecasted to provide a better result for the particular patient being treated. Accordingly, the conventional need for the patient to try this ineffective regimen is thus avoided.

In FIG. 9B, a forecasted response for a proposed dosing regimen of 10 mg/kg given every 8 weeks is shown. As will be noted from FIG. 9B, this proposed dosing regimen forecasts concentrations that are below the target level, but might reflect the second attempt a physician would try in a prior art treatment approach for a patient if the patient failed to respond. In FIG. 9C, a forecasted response for a proposed dosing regimen of 20 mg/kg given every 8 weeks is shown. This dosing regimen might reflect the third attempt that a physician would try to achieve response in a patient in a prior art treatment approach. As can be seen, none of these dosing regimens utilizing doses given every 8 weeks would provide concentrations that were above the target level. As a result of the forecasting provided by the present invention, these ineffective dosing regimens are avoided, and associated deleterious effects to the patient are avoided. Additionally, the patient may be provided with an effective dosing regimen immediately, without the loss of associated time to test these dosing regimens in the patient that are typical of prior art treatment approaches.

Figure 9D:
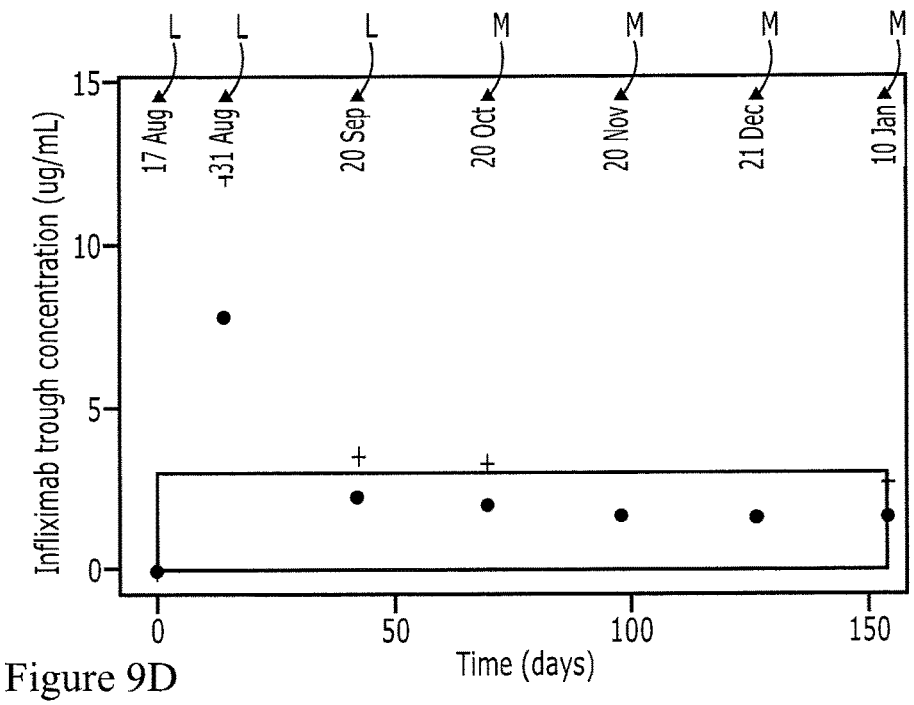
Figure 9E:
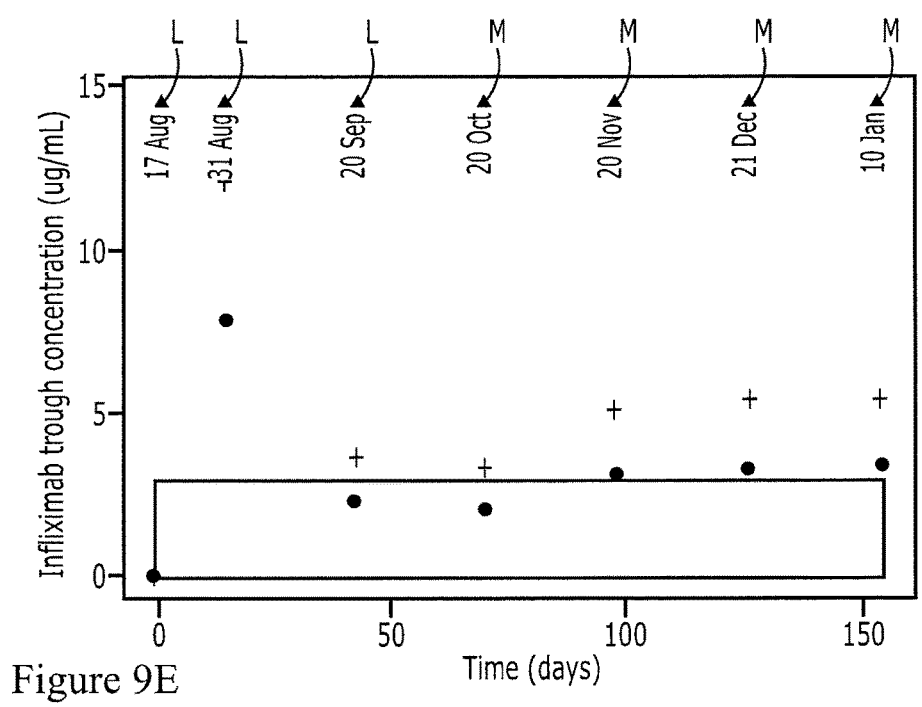
Figure 10A:
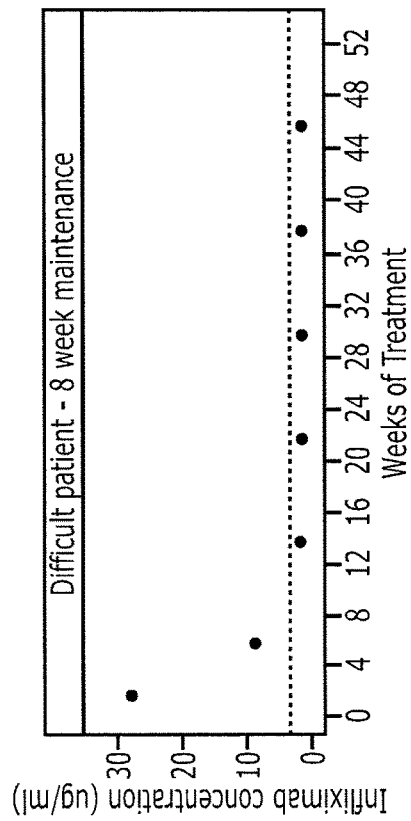
FIGS. 10A-10F are exemplary graphs showing typical-for-covariates and patient-specific forecasts of infliximab blood level concentrations as a function of time, illustrating impacts of varying dose intervals.
Figure 10B:
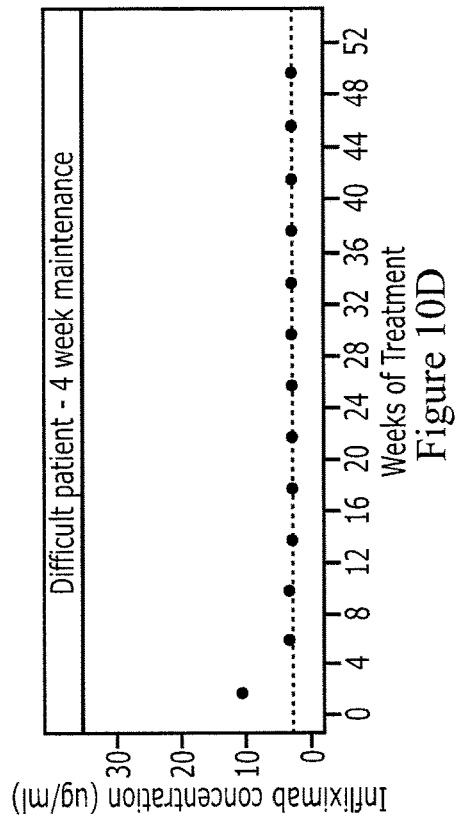
Figure 10C:
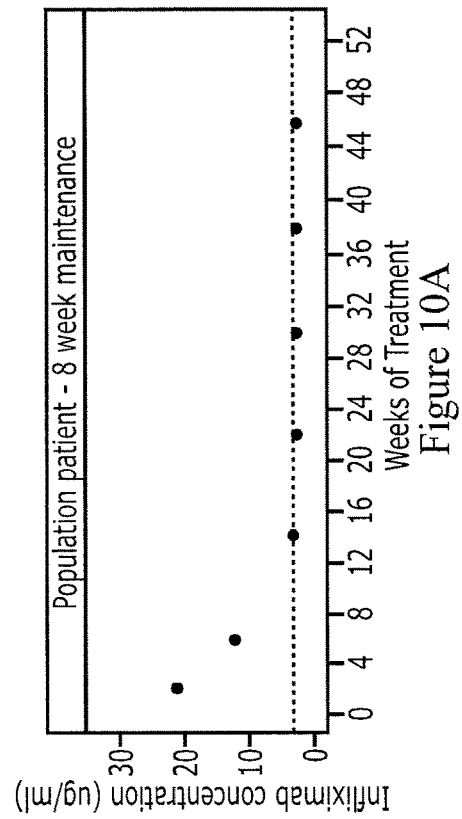
Figure 10D:
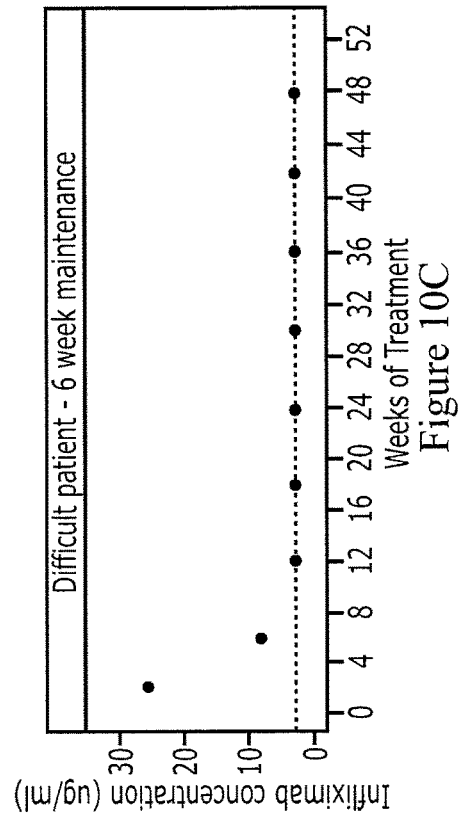
Figures 10E, 10F:
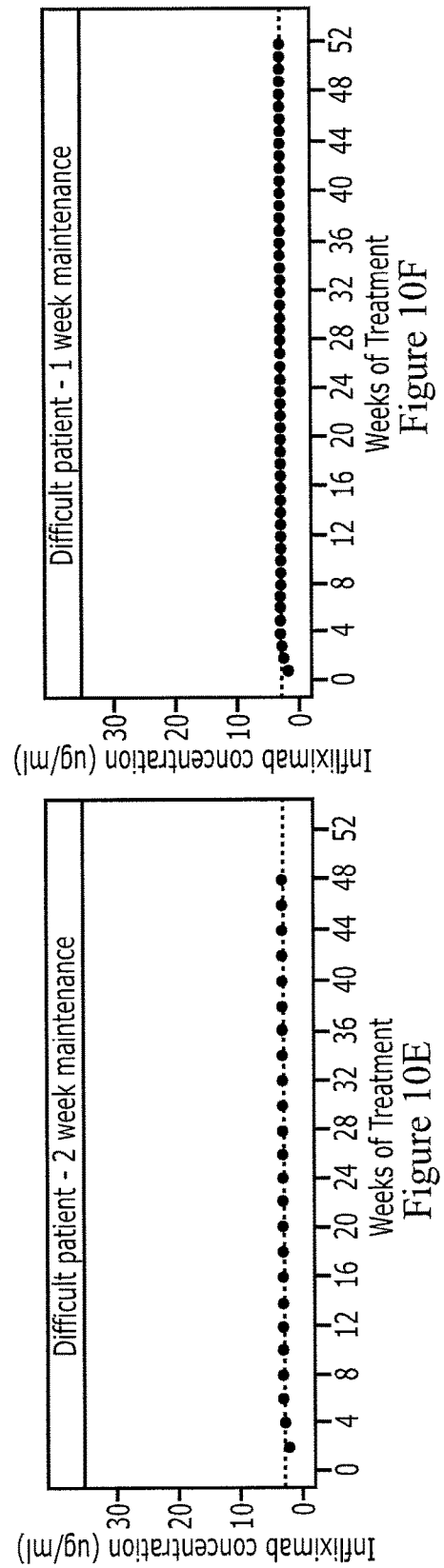

FIGS. 9D and 9E show forecasted responses associated with more frequent dosing regimens. FIG. 9D is a forecasted response for a proposed dosing regimen of 5 mg/kg given every 4 weeks (which is also a viable alternative dose regimen for 5 mg/kg given every 8 weeks). It will be appreciated from FIG. 9D that in this dosing regimen concentrations do not rise above the target trough. Accordingly, this dosing regimen is not satisfactory, and thus not optimal. In FIG. 9E, a forecasted response for a proposed dosing regimen of 10 mg/kg given every 4 weeks is shown. It will be appreciated from FIG. 9E that this dosing regimen provides concentrations that are above the target level. Accordingly, the dosing regimen of FIG. 9E is satisfactory, and would be identified by the system 200 as an acceptable dosing regimen during the automated dose regimen evaluation because the expected concentrations are at or above the target concentration (shaded line).

In accordance with the example of FIGS. 9A-9E, an appropriate dosing regimen would not have been identified by the physician until at least 3-4 dose regimens had been tested in the patient in accordance with prior art treatment techniques. However, the inventive system allows the physician to test the proposed dosing regimens in advance of administration to a patient, identifying dose regimens that are likely to be successful prior to testing them in the patient.

After the system has determined a recommended patient-specific dosing regimen (which may be a list of recommended patient-specific dosing regimens) at step 180, the physician may then browse the recommended patient-specific dosing regimen(s) provided as output by the system, and determine an adjusted dosing regimen for administration to the patient. This may involve reviewing the system's comparison of multiple forecasted responses and selecting a dosing regimen that was forecasted to best meet a treatment objective and is also practicable and feasible. In doing so, the physician may select a dosing regimen from the list, or may modify the recommended patient-specific dosing regimen, in accordance with the physician's judgment. As described above, various considerations may be taken into consideration by the physician and/or the system in determining recommended dosing regimens and/or adjusted dosing regimens.

The physician then directly or indirectly administers the adjusted dosing regimen, as shown at step 182. For example, this may be done by revising a prescription to increase or decrease a medication quantity, to increase or decrease a dosing interval, to change a route of administration, etc., and may be done by the physician directly or indirectly, as discussed above.

As compared with the techniques of the prior art discussed above with reference to FIG. 1, an the initial dosing regimen discussed above with reference to step 168, this patient-specific adjusted dosing regimen is better-personalized to the specific patient to which it is administered because it is based upon an interpretation of the underlying composite mathematical and statistical model(s) as a function of the patient's personal factors, and also the patient's own response to initial treatment. Further, it is based upon forecasted outcomes following evaluations of various doses, dose intervals and routes of administration, as part of the Bayesian forecasting process, and as the result of the updated model account for the observed patient-specific responses and between-subject variability not accounted for in the published models. Accordingly, the adjusted dosing regimen is highly personalized to the specific patient's needs.

After a period of treatment using the adjusted patient-specific dosing regimen, the physician in this exemplary method follows-up with the patient and evaluates the patient's response to the adjusted dosing regimen and determines whether a dose adjustment is warranted, e.g., because the patient response is deficient, as shown at steps 184 and 170. As discussed above, such evaluation may be performed by gathering observations and/or data in a conventional manner. Accordingly, for example, this may involve obtaining laboratory test results reflecting a patient's response to the administered dosing regimen, examining the patient, and/or asking how the patient feels.

If it is determined in step 170 that no dose adjustment is warranted, e.g., because the patient is responding satisfactorily, then the dose adjustment is discontinued and the exemplary method ends, as shown at steps 186 and 188.

If, however, it is determined in step 170 that further dose adjustment is warranted, e.g., because the patient's response is deficient or sub-optimal, then new patient response data may be input to the system and the method may repeat, as shown at steps 170-184.

Because patient condition (disease stage or status) and demographics can change over time, the system can be used to repeatedly update the optimal dose based on each individual patient's updated condition and factors, exposure and/or response behavior so dose can be adjusted to optimal levels throughout the course of therapy, or the therapy can be discontinued if adequate exposure cannot be achieved. Further, the system thus allows a physician to evaluate potential dosing strategies (increasing/decreasing dose, shortening/lengthening dose interval or both) before administering the next dose of drug to the patient. This approach allows a dosing regimen to be optimized (or nearly optimized) within 1-2 dosing regimen cycles, and allows continuous monitoring and selection of appropriate dosing regimens as the patient's condition changes during treatment. This approach is innovative because: it allows the treating physician to provide an initial dosing regimen that is adjusted broadly for known influential factors; the subsequent dosing regimens are adjusted based on each patient's individual behavior; dosing regimens can be optimized rapidly, allowing appropriate drug coverage to be achieved more quickly than the current practice; putative doses can be tested on a computer before administration to the patient; dosing regimens can be adjusted during therapy based on patient condition as needed; and over-dosing and under-dosing can be avoided.

FIG. 3 is a block diagram of an exemplary physician's expert system (PES) (shown logically as a single representative server for ease of illustration) 200 in accordance with the present invention. The PES 200 includes conventional computer hardware storing and/or executing specially-configured computer software that configures the hardware as a particular special-purpose machine having various specially-configured functional sub-components that collectively carry out methods in accordance with the present invention. Accordingly, the PES 200 of FIG. 3 includes a general purpose processor and a bus 204 employed to connect and enable communication between the processor 202 and the components of the PES 200 in accordance with known techniques. The PES 200 typically includes a user interface adapter 206, which connects the processor 202 via the bus 204 to one or more interface devices, such as a keyboard 208, mouse 210, and/or other interface devices 212, which can be any user interface device, such as a touch sensitive screen, digitized entry pad, etc. The bus 204 also connects a display device 214, such as an LCD screen or monitor, to the processor 202 via a display adapter 216. The bus 204 also connects the processor 202 to memory 218, which can include a hard drive, diskette drive, tape drive, etc.

The PES 200 may communicate with other computers or networks of computers, for example via a communications channel, network card or modem 219. The PES 200 may be associated with such other computers in a local area network (LAN) or a wide area network (WAN), and operates as a server in a client/server arrangement with another computer, etc. Such configurations, as well as the appropriate communications hardware and software, are known in the art.

The PES' software is specially configured in accordance with the present invention. Accordingly, as shown in FIG. 3, the PES 200 includes computer-readable, processor-executable instructions stored in the memory for carrying out the methods described herein. Further, the memory stores certain data, e.g. in databases or other data stores shown logically in FIG. 3 for illustrative purposes, without regard to any particular embodiment in one or more hardware or software components. For example, FIG. 3 shows schematically storage in the memory 218 of the PES 200 mathematical model data in Mathematical Model Data Store 218a as a library module, observed response and administered dose information stored in Patient Factor Data Store 218b, composite data models stored in Composite Model Data Store 218c, updated models stored in Updated Model Data Store 218d, and dosing regimen forecast results stored in Dose Regimen Forecast Data Store 218e.

Figure 11:
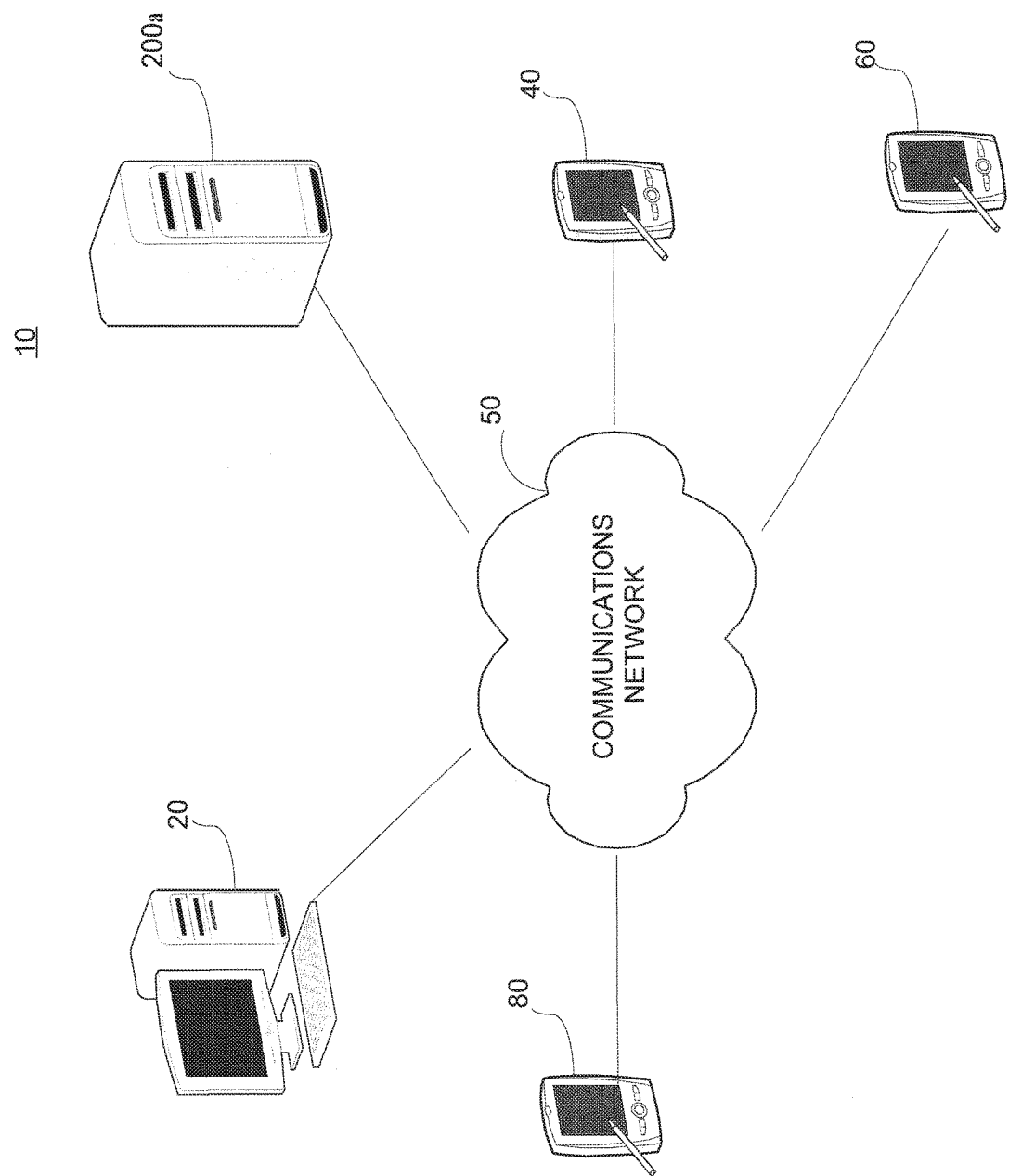
FIG. 11 is a system diagram showing an exemplary network computing environment in which the present invention may be employed.

In an alternative embodiment, the methods and systems described herein are delivered as web services via a network computing model. In such an embodiment, the system may be implemented via a physician/user-operable client device and a centralized server carrying out much of the functionality described above. Such an embodiment is described below with reference to FIG. 11, which is a system diagram showing an exemplary network computing environment 10 in which the present invention may be employed. Referring now to FIG. 11, the network computing environment 10 includes a PES server system 200a operatively connected to a plurality of client devices 20, 40, 60, 80 via a communications network 50, such as the Internet or a proprietary wireless mobile telephone network. The PES server system 200a may include hardware and software conventional for web/application servers, but is further configured in accordance with the present invention to provide the processing functionality described above with reference to PES system 200, and for interacting with the client devices. By way of example, client devices may be a personal computer 20, a mobile telephone/smartphone 40, or a tablet PC, which may have substantially conventional hardware and software for communicating with PES server system 200a via the communications network 50. For example, such devices may be configured for accessing a website or web interface maintained by PES server system 200a, such that the physician/user may operate the client device to provide input and/or receive output described above, and to communicate with the PES server system 200a which performs the associated processing described herein. In these embodiments, the client devices may not require any special-purpose software; rather, all special-purpose software is incorporated into the PES server system 200a, and the client devices are used merely to communicate with inventive PES server system 200a.

Alternatively, the client device may be a smartphone, tablet PC or other computing device 80 configured with a specially-configured native software application running on the client device 80, and communicating with PES server system 200a. In such an embodiment, some or all of the structure and/or processing described above with reference to PES system 200 may be provided at client computing device 80, which may be operate by the user/physician, and which may communicate with PES server system 200a to provide the functionality described herein.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for preparing a patient-specific drug dosing regimen for treating a patient with a medication, using a computerized medication dosing regimen recommendation system, the system comprising a processor, the method comprising:
   receiving data indicative of a first response of the patient to an administered dose of the medication, including medication concentration data measured in blood from the patient;
   accessing, using the processor, a memory;
   selecting, based on at least a portion of the received data, a first model stored in the memory;
   forecasting, based on the selected first model and the medication concentration data measured from the blood of the patient, a patient-specific predicted concentration time profile of the medication, indicative of the patient response to the medication for a plurality of dosing regimens;
   selecting from the plurality of dosing regimens, at least one patient-specific dosing regimen for the medication that achieves a treatment objective based on a desired concentration of the medication in the blood from the patient;
   outputting at least one patient-specific dosing regimen for the medication for the patient;
   receiving data reflecting a response of the patient to the at least one patient-specific dosing regimen for the medication;
   updating the first model, based on the received data reflecting the response of the patient to the at least one patient-specific dosing regimen for the medication;
   calculating, based on the updated first model, at least one updated dosing regimen for the medication to reach the treatment objective for the patient; and
   outputting the at least one updated dosing regimen for the medication for the patient to treat the disease of the patient; and
   administering the at least one updated dosing regimen or a modified version of the at least one updated dosing regimen.

2. The method of claim 1, wherein the method further comprises:
   receiving a signal indicative of the treatment objective for the specific patient,
   wherein the first model is periodically updated until the treatment objective is achieved.

3. The method of claim 2, wherein the memory includes a database, and wherein the memory is stored in the computerized medication dosing regimen recommendation system further comprises the memory and a database stored in the memory.

4. The method of claim 3, wherein the database stores the data indicative of characteristics of the specific patient, and wherein the processor connects to the memory through a bus.

5. The method of claim 2, wherein the step of selecting the first model comprises:
   comparing the received data indicative of a first response of the patient to an administered dose of the medication, including medication concentration data measured in blood from the patient to patient characteristics associated with a plurality of models;
   selecting a model from the plurality of models with patient characteristics that match the received data; and
   outputting the determined model.

6. The method of claim 2, wherein the treatment objective is a target profile representing a physiologic response of the specific patient to the at least one dosing regimen over time.

7. The method of claim 2, wherein the treatment objective comprises maintaining a measurement above a therapeutic threshold for a period of time.

8. The method of claim 7, wherein the treatment objective comprises maintaining the measurement below a second therapeutic threshold for the period of time.

9. The method of claim 7, wherein the therapeutic threshold is stored in the memory.

10. The method of claim 1, wherein the received data includes at least one of: a body size indicator, gender, race, disease stage, disease status, prior therapy, concomitantly administered drugs, concomitant diseases, demographic information, and laboratory test result information.

11. The method of claim 1, wherein the received data includes at least one of: a drug concentration level, a blood pressure reading, and a hematocrit level.

12. The method of claim 1, wherein the computerized medication dosing regimen recommendation system comprises a microprocessor communicatively coupled to the memory.

13. The method of claim 12, wherein the computerized medication dosing regimen recommendation system includes a database stored in the memory, the database being accessible by the microprocessor and storing information indicative of dosing regimens associated with the medication.

14. The method of claim 1, wherein updating the first model comprises:
adjusting the first model to fit the response data.

15. The method of claim 1, wherein the first model is one of: a pharmacokinetic (PK) model, a pharmacodynamic (PD) model, and an exposure/response model.

16. The method of claim 14, further comprising:
outputting a subset of the plurality of dosing regimens as updated dosing regimens.

17. The method of claim 1, wherein calculating the at least one updated dosing regimen comprises:
forecasting a patient response not specific to any particular patient for each of a first plurality of dosing regimens; and
selecting at least one dosing regimen of the first plurality of dosing regimens according to predefined logic,
wherein the predefined logic determines the selection of the at least one dosing regimen to find a minimum of a plurality of objective functions.

18. The method of claim 1, wherein calculating the at least one updated dosing regimen comprises:
selecting, based on the characteristics of the specific patient and predefined logic, at least one dosing regimen corresponding to a minimum of an objective function.

19. A method of treatment with a medication, using a computerized medication dosing regimen recommendation system, the system comprising a processor, the method comprising:
receiving a treatment objective for a specific patient;
receiving data indicative of characteristics of the specific patient;
accessing, using the processor, a memory;
selecting, based on at least a portion of the data indicative of the characteristics of the specific patient, a first model stored in the memory;
forecasting, based on the selected first model and medication concentration data measured from the blood of the specific patient, a patient-specific predicted concentration time profile of the medication, indicative of a response of the specific patient to the medication for a plurality of dosing regimens;
selecting from the plurality of dosing regimens, at least one patient-specific dosing regimen for the medication that achieves a treatment objective based on a desired concentration of the medication in the blood from the patient;
outputting at least one dosing regimen;
administering the at least one dosing regimen to the specific patient;
receiving data reflecting a response of the patient to the administered at least one dosing regimen;
updating the selected first model, based on the received data reflecting the response of the specific patient;
calculating, based on the updated first model, at least one updated dosing regimen to reach the treatment objective;
outputting the at least one updated dosing regimen; and
administering the at least one updated dosing regimen,
wherein the first model is periodically updated until the treatment objective is achieved.

20. A method for treating a specific patient with a medication, the method comprising:
setting a treatment objective for the specific patient;
using a computerized medication dosing regimen recommendation system to achieve the treatment objective for the specific patient, the computerized medication doing regimen recommendation system configured to:
receive data indicative of a first response of the patient to an administered dose of the medication, including medication concentration data measured in blood from the patient;
access, using the processor, a memory;
select, based on at least a portion of the received data, a first model stored in the memory;
forecast, based on the selected first model and the medication concentration data measured from the blood of the patient, a patient-specific predicted concentration time profile of the medication, indicative of the patient response to the medication for a plurality of dosing regimens;
select from the plurality of dosing regimens, at least one patient-specific dosing regimen for the medication that achieves a treatment objective based on a desired concentration of the medication in the blood from the patient;
output at least one patient-specific dosing regimen for the medication for the patient;
receive data reflecting a response of the patient to the at least one patient-specific dosing regimen for the medication;
update the first model, based on the received data reflecting the response of the patient to the at least one patient-specific dosing regimen for the medication;
calculate, based on the updated first model, at least one updated dosing regimen for the medication to reach the treatment objective for the patient; and
output the at least one updated dosing regimen for the medication for the patient to treat the disease of the patient; and
administering the at least one updated dosing regimen or a modified version of the at least one updated dosing regimen.

* * * * *